United States Patent
Czaplewski et al.

(10) Patent No.: US 12,161,750 B2
(45) Date of Patent: *Dec. 10, 2024

(54) ANTIBIOTIC FORMULATIONS FOR LOWER BACK PAIN

(71) Applicant: Persica Pharmaceuticals Ltd., Canterbury (GB)

(72) Inventors: Lloyd Czaplewski, Canterbury (GB); Sarah Guest, Canterbury (GB)

(73) Assignee: Persica Pharmaceuticals Ltd., Canterbury (GB)

(*) Notice: Subject to any disclaimer, the term of this patent is extended or adjusted under 35 U.S.C. 154(b) by 0 days.

This patent is subject to a terminal disclaimer.

(21) Appl. No.: 17/969,554

(22) Filed: Oct. 19, 2022

(65) Prior Publication Data

US 2023/0149297 A1 May 18, 2023

Related U.S. Application Data

(63) Continuation of application No. 17/142,559, filed on Jan. 6, 2021, now abandoned, which is a continuation of application No. 16/461,434, filed as application No. PCT/GB2017/053447 on Nov. 16, 2017, now abandoned.

(60) Provisional application No. 62/423,112, filed on Nov. 16, 2016.

(51) Int. Cl.
| | |
|---|---|
| *A61K 9/00* | (2006.01) |
| *A61K 9/14* | (2006.01) |
| *A61K 31/5377* | (2006.01) |
| *A61K 38/14* | (2006.01) |
| *A61K 47/10* | (2017.01) |
| *A61K 47/34* | (2017.01) |
| *A61K 49/04* | (2006.01) |
| *A61L 27/18* | (2006.01) |
| *A61L 27/52* | (2006.01) |
| *A61L 27/54* | (2006.01) |
| *A61L 27/58* | (2006.01) |
| *A61P 25/04* | (2006.01) |
| *A61P 29/00* | (2006.01) |
| *A61P 31/00* | (2006.01) |
| *A61P 31/04* | (2006.01) |

(52) U.S. Cl.
CPC .......... *A61K 9/0024* (2013.01); *A61K 9/0019* (2013.01); *A61K 9/146* (2013.01); *A61K 31/5377* (2013.01); *A61K 38/14* (2013.01); *A61K 47/10* (2013.01); *A61K 47/34* (2013.01); *A61K 49/0438* (2013.01); *A61K 49/0457* (2013.01); *A61K 49/0461* (2013.01); *A61L 27/18* (2013.01); *A61L 27/52* (2013.01); *A61L 27/54* (2013.01); *A61L 27/58* (2013.01); *A61P 25/04* (2018.01); *A61P 29/00* (2018.01); *A61P 31/00* (2018.01); *A61P 31/04* (2018.01); *A61K 2300/00* (2013.01); *A61L 2300/406* (2013.01); *A61L 2400/06* (2013.01); *A61L 2430/38* (2013.01)

(58) Field of Classification Search
None
See application file for complete search history.

(56) References Cited

U.S. PATENT DOCUMENTS

| | | | |
|---|---|---|---|
| 4,153,512 A * | 5/1979 | Messner | C12M 23/12 435/33 |
| 4,330,529 A * | 5/1982 | Imanaka | C07F 9/3808 987/168 |
| 5,628,734 A | 5/1997 | Hatfalvi | |
| 5,702,717 A | 12/1997 | Cha et al. | |
| 6,444,813 B2 | 9/2002 | Bergren | |
| 6,461,607 B1 * | 10/2002 | Farmer | A61P 31/12 424/93.46 |
| 6,500,153 B1 | 12/2002 | Sheppard et al. | |
| 6,559,305 B1 | 5/2003 | Bergren | |
| 6,787,568 B1 * | 9/2004 | Mihalik | A61K 31/573 514/618 |
| 7,259,225 B2 | 8/2007 | Song et al. | |
| 7,367,961 B2 | 5/2008 | DiMauro et al. | |
| 7,718,799 B2 | 5/2010 | Rao et al. | |
| 8,112,159 B2 | 2/2012 | Harris et al. | |
| 9,364,544 B2 | 6/2016 | Pierre et al. | |
| 9,364,545 B2 | 6/2016 | Jhan et al. | |
| 11,517,574 B2 * | 12/2022 | Czaplewski | A61K 9/0024 |
| 2001/0051621 A1 | 12/2001 | Bergren | |
| 2001/0056206 A1 | 12/2001 | Lorenzini et al. | |
| 2002/0028197 A1 | 3/2002 | Fitchett | |
| 2005/0143678 A1 | 6/2005 | Schwarz et al. | |
| 2007/0104785 A1 | 5/2007 | Navale et al. | |

(Continued)

FOREIGN PATENT DOCUMENTS

| | | |
|---|---|---|
| CN | 104586768 A | 5/2011 |
| CN | 102988274 A | 3/2013 |

(Continued)

OTHER PUBLICATIONS

Wikipedia webpage https://en.wikipedia.org/wiki/Otitis_media (year unknown).*
Escobar-Chavez et al ("Applications of Thermoreversible Pluronic F-127 Gels in Pharmaceutical Formulations", J. Pharm Pharmaceut Sci, vol. 9(3) (2006), p. 339-358) (Year: 2006).*
Lee et al ("The Effect of Poloxamer 407-Based Hydrogel on the Osteoinductivity of Demineralized Bone Matrix", Clinics in Orthopedic Surgery, vol. 6 (2014), p. 455-461) (Year: 2014).*
Lee et al ("Intradiscal drug delivery system for the treatment of low back pain", Journal of Biomedical Materials Research, Part A, (2009), p. 378-385) (Year: 2009).*

(Continued)

*Primary Examiner* — Sin J Lee
(74) *Attorney, Agent, or Firm* — Wolf, Greenfield & Sacks, P.C.

(57) ABSTRACT

The present invention relates to injectable compositions. More particularly, the present disclosure relates to injectable, thermogelling hydrogel formulations comprising at least one antibiotic for relieving and/or treating low back pain.

21 Claims, 4 Drawing Sheets

(56) References Cited

U.S. PATENT DOCUMENTS

| | | | |
|---|---|---|---|
| 2008/0319191 | A1 | 12/2008 | Aronhime et al. |
| 2010/0036000 | A1 | 2/2010 | Lichter et al. |
| 2010/0098762 | A1 | 4/2010 | Han et al. |
| 2011/0076231 | A1 | 3/2011 | Schwarz et al. |
| 2012/0263797 | A1 | 10/2012 | D'Agostino et al. |
| 2012/0277199 | A1 | 11/2012 | Ye et al. |
| 2013/0164224 | A1 | 6/2013 | Kim et al. |
| 2013/0177603 | A1 | 7/2013 | Gutierro Aduriz et al. |
| 2013/0195988 | A1 | 8/2013 | Duan et al. |
| 2013/0230495 | A1 | 9/2013 | Chiou et al. |
| 2014/0256617 | A1 | 9/2014 | Overstreet et al. |
| 2014/0275977 | A1 | 9/2014 | Curley et al. |
| 2014/0302051 | A1 | 10/2014 | Askari et al. |
| 2015/0025106 | A1 | 1/2015 | Kwon et al. |
| 2016/0030581 | A1 | 2/2016 | Gaudriault |
| 2016/0243026 | A1 | 8/2016 | Pathak |
| 2016/0310699 | A1 | 10/2016 | Al-Jilaihawi |
| 2017/0008919 | A1 | 1/2017 | Sheng et al. |
| 2017/0290948 | A1 | 10/2017 | Schwarz et al. |
| 2018/0086788 | A1* | 3/2018 | Kim .................. A23L 33/40 |
| 2019/0343761 | A1 | 11/2019 | Czaplewski et al. |
| 2020/0352952 | A1 | 11/2020 | Czaplewski et al. |
| 2021/0128454 | A1 | 5/2021 | Czaplewski et al. |
| 2023/0143410 | A1 | 5/2023 | Czaplewski et al. |

FOREIGN PATENT DOCUMENTS

| | | |
|---|---|---|
| CN | 105682640 A | 6/2016 |
| CN | 109982729 B | 4/2022 |
| EP | 3081232 A1 | 10/2016 |
| JP | 2009-538285 A | 11/2009 |
| JP | 2013-508116 A | 3/2013 |
| JP | 2013-508381 A | 3/2013 |
| JP | 2016-533354 A | 10/2016 |
| JP | 2020-500221 A | 1/2020 |
| JP | 7101694 B2 | 7/2022 |
| RU | 2495662 C2 | 10/2013 |
| WO | WO 2001/057035 A1 | 8/2001 |
| WO | WO 2002/30395 A1 | 4/2002 |
| WO | WO 2004/084703 A2 | 10/2004 |
| WO | WO 2006/110155 A1 | 10/2006 |
| WO | WO 2006/118804 A1 | 11/2006 |
| WO | WO 2007/026369 A1 | 3/2007 |
| WO | WO 2007/083875 A2 | 7/2007 |
| WO | WO 2007/137653 A1 | 12/2007 |
| WO | WO 2011/049958 A1 | 4/2011 |
| WO | WO 2011/056528 A2 | 5/2011 |
| WO | WO 2011/140519 A2 | 11/2011 |
| WO | WO 2014/013498 A1 | 1/2014 |
| WO | WO 2015/012899 A1 | 1/2015 |
| WO | WO 2015/048988 A1 | 4/2015 |
| WO | WO 2015/059623 A1 | 4/2015 |
| WO | WO 2015/073066 A1 | 5/2015 |
| WO | WO 2017/019440 A1 | 2/2017 |
| WO | WO 2018/091895 A1 | 5/2018 |
| WO | WO 2019/060869 A1 | 3/2019 |

OTHER PUBLICATIONS

Pharmaceutical Processing ("Sterilization of Injectable Components", internet article published on Oct. 21, 2015 and obtained at the website: https://www.pharmaceuticalprocessingworld.com/sterilization-of-injectable-components/ ) (Year: 2015).*

Taylor et al ("Evaluation of the Stability of Linezolid in Aqueous Solution and Commonly Used Intravenous Fluids", Drug Design, Development and Therapy, vol. 11 (2017) p. 2087-2097) (Year: 2017).*

Birchard ("Transthoracic Needle Biopsy", Semin Intervent Radiol. vol.28(1) (Mar. 2011), p. 87-97) (Year: 2011).*

U.S. Appl. No. 16/461,434, filed May 16, 2019, Czaplewski et al.

U.S. Appl. No. 17/142,559, filed Jan. 6, 2021, Czaplewski et al.

U.S. Appl. No. 16/764,468, filed May 15, 2020, Czaplewski et al.

U.S. Appl. No. 17/967,783, filed Oct. 17, 2022, Czaplewski et al.

PCT/GB2017/053447, Feb. 7, 2018, International Search Report and Written Opinion.

PCT/GB2017/053447, May 31, 2019, International Preliminary Report on Patentability.

PCT/GB2018/053319, Feb. 14, 2019, International Search Report and Written Opinion.

PCT/GB2018/053319, May 28, 2020, International Preliminary Report on Patentability.

International Search Report and Written Opinion for Application No. PCT/GB2017/053447, mailed Feb. 7, 2018.

International Preliminary Report on Patentability for Application No. PCT/GB2017/053447, mailed May 31, 2019.

International Search Report and Written Opinion for Application No. PCT/GB2018/053319, mailed Feb. 14, 2019.

International Preliminary Report on Patentability for Application No. PCT/GB2018/053319, mailed May 28, 2020.

Agarwal et al., Bacteriologic culture of excised intervertebral disc from immunocompetent patients undergoing single level primary lumbar microdiscectomy. J Spinal Disord Tech. Aug. 2011;24(6):397-400. doi: 10.1097/BSD.0b013e3182019f3a.

Ahern, Biochemical, Reagent Kits Offer Scientists Good Return on Investment. The Scientist. 1995. Retrieved from the internet: <http://www.the-scientist.library.upenn.edu/yr1995/july/tools_950724.html>.

Albert et al., Antibiotic treatment in patients with chronic low back pain and vertebral bone edema (Modic type 1 changes): a double-blind randomized clinical controlled trial of efficacy. Eur Spine J. Apr. 2013;22(4):697-707. doi: 10.1007/s00586-013-2675-y. Epub Feb. 13, 2013.

Albert et al., Antibiotic treatment in patients with low-back pain associated with Modic changes Type 1 (bone oedema): a pilot study. Br J Sports Med. Dec. 2008;42(12):969-73. doi: 10.1136/bjsm.2008.050369. Epub Aug. 21, 2008.

Albert et al., Does nuclear tissue infected with bacteria following disc herniations lead to Modic changes in the adjacent vertebrae?. Eur Spine J. Apr. 2013;22(4):690-6. doi: 10.1007/s00586-013-2674-z. Epub Feb. 10, 2013.

Albert et al., Modic changes following lumbar disc herniation. Eur Spine J. Jul. 2007;16(7):977-82. doi: 10.1007/s00586-007-0336-8. Epub Mar. 3, 2007.

Bruins et al., In vitro study of the antimicrobial effects of radiological contrast agents used in arthrography. J Bone Joint Surg Br. Jan. 2011;93(1):126-30. doi: 10.1302/0301-620X.93B1.24968.

Capoor et al., Prevalence of Propionibacterium acnes in Intervertebral Discs of Patients Undergoing Lumbar Microdiscectomy: a Prospective Cross-Sectional Study. PLoS One. Aug. 18, 2016;11(8):e0161676. doi: 10.1371/journal.pone.0161676. eCollection 2016.

Capoor et al., Propionibacterium acnes biofilm is present in intervertebral discs of patients undergoing microdiscectomy. PLos One. Apr. 3, 2017;12(4):e0174518. doi: 10.1371/journal.pone.0174518. eCollection 2017.

Chen et al., Modic Changes and Disc Degeneration Caused by Inoculation of Propionibacterium acnes inside Intervertebral Discs of Rabbits: a Pilot Study. Biomed Res Int. 2016: 2016;2016:9612437. doi: 10.1155/2016/9612437. Epub Jan. 26, 2016.

Chenite et al., Novel injectable neutral solutions of chitosan form biodegradable gels in situ. Biomaterials. Nov. 2000;21(21):2155-61. doi: 10.1016/s0142-9612(00)00116-2.

Communication pursuant to Article 94(3) EPC issued Apr. 14, 2021 in counterpart European Application No. 18808077.4.

Communication pursuant to Article 94(3) EPC issued Nov. 24, 2020 in corresponding Application No. 17809337.3.

Corsia et al., Low virulence bacterial infections of intervertebral discs and the resultant spinal disease processes. Abstract from Scoliosis Research Society (SRS) annual meeting. 2003. 1 page.

Dawson et al., The effect of contrast media on the growth of bacteria. Br J Radiol. Nov. 1983;56(671):809-15. doi: 10.1259/0007-1285-56-671-809.

Dryden, Linezolid pharmacokinetics and pharmacodynamics in clinical treatment. J Antimicrob Chemother. May 2011;66 Suppl 4:iv7-iv15. doi: 10.1093/jac/dkr072.

(56) References Cited

OTHER PUBLICATIONS

Dudli et al., Inflammatory response of disc cells against Propionibacterium acnes depends on the presence of lumbar Modic changes. Eur Spine J. May 2018;27(5):1013-1020. doi: 10.1007/s00586-017-5291-4. Epub Sep. 7, 2017.
Dudli et al., Propionibacterium acnes infected intervertebral discs cause vertebral bone marrow lesions consistent with Modic changes. J Orthop Res. Aug. 2016;34(8):1447-55. doi: 10.1002/jor.23265. Epub Aug. 3, 2016.
Falagas et al., Linezolid for the treatment of adults with bone and joint infections. Int J Antimicrob Agents. Mar. 2007;29(3):233-9. doi: 10.1016/j.ijantimicag.2006.08.030. Epub Jan. 3, 2007.
Fayad et al., Relation of inflammatory modic changes to intradiscal steroid injection outcome in chronic low back pain. Eur Spine J. Jul. 2007;16(7):925-31. doi: 10.1007/s00586-006-0301-y. Epub Jan. 10, 2007.
Fleege et al., Systemische und lokale Antibiotikatherapie bei konservativ und operativ behandelten Spondylodiszitiden. Der Orthopade, Springer-Verlag. Aug. 24, 2012; 41(9): 727-735.
Gans et al., Adjunctive vancomycin powder in pediatric spine surgery is safe. Spine (Phila Pa 1976). Sep. 1, 2013;38(19):1703-7. doi: 10.1097/BRS.0b013e31829e05d3.
Gaudin et al., A delivery system of linezolid to enhance the MRSA osteomyelitis prognosis: in vivo experimental assessment. Eur J Clin Microbiol Infect Dis. Feb. 2013;32(2):195-8. doi: 10.1007/s10096-012-1731-6. Epub Aug. 25, 2012.
Gautier et al., In vitro characterization of calcium phosphate biomaterial loaded with linezolid for osseous bone defect implantation. J Biomater Appl. Mar. 2012;26(7):811-28. doi: 10.1177/0885328210381535. Epub Sep. 28, 2010.
Gong et al., Thermosensitive polymeric hydrogels as drug delivery systems. Curr Med Chem. 2013;20(1):79-94.
Jensen et al., Vertebral endplate signal changes (Modic change): a systematic literature review of prevalence and association with non-specific low back pain. Eur Spine J. Nov. 2008;17(11):1407-22. doi: 10.1007/s00586-008-0770-2. Epub Sep. 12, 2008.
Karolewicz et al., [In vitro evaluation of the gels properties prepared thermosensitive polymers as vehicles for administration substance by injection]. Polim Med. 2011;41(4):3-15.
Kjaer et al., Magnetic resonance imaging and low back pain in adults: a diagnostic imaging study of 40-year-old men and women. Spine (Phila Pa 1976). May 15, 2005;30(10):1173-80. doi: 10.1097/01.brs.0000162396.97739.76.
Klessig et al., The use of intradiscal antibiotics for discography: an in vitro study of gentamicin, cefazolin, and clindamycin. Spine (Phila Pa 1976). Aug. 1, 2003;28(15):1735-8. doi: 10.1097/01.BRS.0000087301.71177.85.
Knezevic et al., Treatment of chronic low back pain—new approaches on the horizon. J Pain Res. May 10, 2017;10:1111-1123. doi: 10.2147/JPR.S132769. eCollection 2017.
Komatsu et al., Penetration of linezolid into rabbit intervertebral discs and surrounding tissues. Eur Spine J. Dec. 2010;19(12):2149-55. doi: 10.1007/s00586-010-1548-x. Epub Aug. 9, 2010.
Langer et al., In vitro assessment of the antibiotic efficacy of contrast media and antibiotics and their combinations at various dilutions. Br J Radiol. May 2010;83(989):394-400. doi: 10.1259/bjr/62389328. Epub Aug. 18, 2009.
Lee et al., Intradiscal drug delivery system for the treatment of low back pain. J Biomed Mater Res A. Jan. 2010;92(1):378-85. doi: 10.1002/jbm.a.32377.
Lee et al., Regional delivery of vancomycin using pluronic F-127 to inhibit methicillin resistant *Staphylococcus aureus* (MRSA) growth in chronic otitis media in vitro and in vivo. J Control Release. Apr. 16, 2004;96(1):1-7. doi: 10.1016/j.jconrel.2003.12.029.
Macphail, Low Back Pain, Modic Changes and Bacterial Infections. Feb. 23, 2013. Last accessed Jan. 17, 2023. http://www.kieranmacphail.com/2013/02/23/low-back-pain-modic-changes-and-bacterial-infections/.
Modic et al., Degenerative disk disease: assessment of changes in vertebral body marrow with MR imaging. Radiology. Jan. 1988;166(1 Pt 1):193-9. doi: 10.1148/radiology.166.1.3336678.
Nazipi et al., The Skin Bacterium Propionibacterium acnes Employs Two Variants of Hyaluronate Lyase with Distinct Properties. Microorganisms. Sep. 12, 2017;5(3):57. doi: 10.3390/microorganisms5030057.
Nguyen et al., Injectable biodegradable hydrogels. Macromol Biosci. Jun. 11, 2010;10(6):563-79. doi: 10.1002/mabi.200900402.
Nie et al., Thermoreversible Pluronic F127-based hydrogel containing liposomes for the controlled delivery of paclitaxel: in vitro drug release, cell cytotoxicity, and uptake studies. Int J Nanomedicine. 2011;6:151-66. doi: 10.2147/IJN.S15057. Epub Jan. 19, 2011.
Office Action issued Apr. 23, 2021 in corresponding Chinese Application No. 201780070772.4.
Office Action issued Dec. 7, 2021 in corresponding Japanese Application No. 2019- 547196.
Office Action issued Nov. 12, 2021 in corresponding Russian Application No. 2020115866.
Office Action issued Sep. 8, 2021 in corresponding Chinese Application No. 201780070772.4.
Olsson et al., Antibiotic susceptibility in prostate-derived Propionibacterium acnes isolates. APMIS. Oct. 2012;120(10):778-85. doi: 10.1111/j.1600-0463.2012.02905.x. Epub Apr. 28, 2012.
Pandit et al., Gelation of Pluronic F127-polyethylene glycol mixtures: relationship to PEG molecular weight. Drug Dev Ind Pharm. Feb. 1998;24(2):183-6. doi: 10.3109/03639049809085605.
Radivojsa et al., Thermoreversible in situ gelling poloxamer-based systems with chitosan nanocomplexes for prolonged subcutaneous delivery of heparin: design and in vitro evaluation. Eur J Pharm Sci. Sep. 27, 2013;50(1):93-101. doi: 10.1016/j.ejps.2013.03.002. Epub Mar. 21, 2013.
Rybak et al., Therapeutic monitoring of vancomycin in adult patients: a consensus review of the American Society of Health-System Pharmacists, the Infectious Diseases Society of America, and the Society of Infectious Diseases Pharmacists. Am J Health Syst Pharm. Jan. 1, 2009;66(1):82-98. doi: 10.2146/ajhp080434.
Schmolka, Artificial skin. I. Preparation and properties of pluronic F-127 gels for treatment of burns. J Biomed Mater Res. Nov. 1972;6(6):571-82. doi: 10.1002/jbm.820060609.
Search Report issued Nov. 12, 2021 in corresponding Russian Application No. 2020115866.
Search Report issued Nov. 12, 2021 in corresponding Singapore Application No. 11202003537T.
Shan et al., Propionibacterium acnes Incubation in the Discs Can Result in Time-Dependent Modic Changes: A Long-Term Rabbit Model. Spine (Phila Pa 1976). Nov. 1, 2017;42(21):1595-1603. doi: 10.1097/BRS.0000000000002192.
Shan et al., The Influence of Direct Inoculation of Propionibacterium acnes on Modic Changes in the Spine: Evidence from a Rabbit Model. J Bone Joint Surg Am. Mar. 15, 2017;99(6):472-481. doi: 10.2106/JBJS.16.00146.
Shibayama et al., Supplemental Antibiotic Injections into the Disc Eradicate Lumbar Pyogenic Spondylodiscitis and Reduce Residual Lumbago. J Spine. 2018; 7(1): 1-7. DOI: 10.4172/2165-7939.1000406.
Slaby et al., Is IL-1β Further Evidence for the Role of Propionibacterium acnes in Degenerative Disc Disease? Lessons From the Study of the Inflammatory Skin Condition Acne Vulgaris. Front Cell Infect Microbiol. Aug. 14, 2018;8:272. doi: 10.3389/fcimb.2018.00272. eCollection 2018.
Stirling et al., Association between sciatica and Propionibacterium acnes. Lancet. Jun. 23, 2001;357(9273):2024-5. doi: 10.1016/S0140-6736(00)05109-6.
Sweet et al., Intrawound application of vancomycin for prophylaxis in instrumented thoracolumbar fusions: efficacy, drug levels, and patient outcomes. Spine (Phila Pa 1976). Nov. 15, 2011;36(24):2084-8. doi: 10.1097/BRS.0b013e3181ff2cb1.
Urquhart et al., Could low grade bacterial infection contribute to low back pain? A systematic review. BMC Med. Jan. 22, 2015;13:13. doi: 10.1186/s12916-015-0267-x.
Veyries et al., Control of staphylococcal adhesion to polymethylmethacrylate and enhancement of susceptibility to anti-

(56) References Cited

OTHER PUBLICATIONS biotics by poloxamer 407. Antimicrob Agents Chemother. Apr. 2000;44(4):1093-6. doi: 10.1128/AAC.44.4.1093-1096.2000.
Veyries et al., Controlled release of vancomycin from poloxamer 407 gels. Int J Pharm. Dec. 10, 1999;192(2):183-93. doi: 10.1016/s0378-5173(99)00307-5.
Waddell, 1987 Volvo award in clinical sciences. A new clinical model for the treatment of low-back pain. Spine (Phila Pa 1976). Sep. 1987;12(7):632-44. doi: 10.1097/00007632-198709000-00002.
Written Opinion issued Nov. 12, 2021 in corresponding Singapore Application No. 11202003537T.
Zamora et al., Effect of Propionibacterium acnes (PA) injection on intervertebral disc degeneration in a rat model: Does it mimic modic changes? Orthop Traumatol Surg Res. Sep. 2017;103(5):795-799. doi: 10.1016/j.otsr.2017.04.005. Epub May 25, 2017.
Zheng et al., Determination and Correlation of Solubility of linezolid form II in different pure and binary solvents. Fluid Phase Equilibria. 2017; 432: 18-27.
Agarwal et al., Results of Bacterial Culture from Surgically Excised Intervertebral Disc in 52 Patients Undergoing Primary Lumbar Microdiscectomy at a Single Level. Spine J. 2010; 10: S45-S46.
Chen et al., Overview: the role of Propionibacterium acnes in nonpyogenic intervertebral discs. Int Orthop. Jun. 2016;40(6):1291-8. doi: 10.1007/s00264-016-3115-5. Epub Jan. 28, 2016.
Modic et al., Imaging of degenerative disk disease. Radiology. Jul. 1988;168(1):177-86. doi: 10.1148/radiology.168.1.3289089.
Tsiolis et al., Experimental osteomyelitis caused by methicillin-resistant *Staphylococcus aureus* treated with a polylactide carrier releasing linezolid. Surg Infect (Larchmt). Apr. 2011;12(2):131-5. doi: 10.1089/sur.2010.050. Epub Feb. 24, 2011.
Bouchot et al., Clinical experience with a novel thermosensitive temporary coronary artery occluder (LeGoo). Ann Thorac Surg. Jun. 2010;89(6):1912-7. doi: 10.1016/j.athoracsur.2010.03.015.
Costeron et al., How Bacteria Stick. Sci Am. Jan. 1978;238(1):86-95. doi: 10.1038/scientificamerican0178-86.
Elabd et al., Intra-discal injection of autologous, hypoxic cultured bone marrow-derived mesenchymal stem cells in five patients with chronic lower back pain: a long-term safety and feasibility study. J Transl Med. Sep. 1, 2016;14(1):253. doi: 10.1186/s12967-016-1015-5.
Gristina et al., Bacterial adherence to biomaterials and tissue. The significance of its role in clinical sepsis. J Bone Joint Surg Am. Feb. 1985;67(2):264-73.
Gristina, Biomaterial-centered infection: microbial adhesion versus tissue integration. Science. Sep. 25, 1987;237(4822):1588-95. doi: 10.1126/science.3629258.
Jones et al., Preventing and Treating Adverse Events of Injectable Fillers: Evidence-Based Recommendations From the American Society for Dermatologic Surgery Multidisciplinary Task Force. Dermatol Surg. Feb. 1, 2021;47(2):214-226. doi: 10.1097/DSS.0000000000002921.
Lacombe, Introducing VOLUX UX: The First FDA Approved Filler for Jawline Definition. Artemedica. Nov. 17, 2022. Accessed at: https://www.artemedica.com/fda-approves-juvederm-volux/. Last accessed: Apr. 3, 2024.
Lu et al., Injectable hyaluronic-acid-doxycycline hydrogel therapy in experimental rabbit osteoarthritis. BMC Vet Res. Apr. 10, 2013;9:68. doi: 10.1186/1746-6148-9-68.
No Author Listed, DAC® Defensive Antibacterial Coating Brochure. Novagenit. 2017. 8 Pages.
No Author Listed, FDA Approves JUVÉDERM® VOLUX™ XC for Improvement of Jawline Definition. Aug. 3, 2022. Accessed at: https://www.prnewswire.com/news-releases/fda-approves-juvederm-volux-xc-for-improvement-of-jawline-definition-301598563.html. Last accessed: Apr. 3, 2024.
No Author Listed, Instructions for Use Synvisc® (hylan G-F 20). Genzyme Corporation. Date of revision: Dec. 3, 2014. Version 1.1. 7 pages.
No Author Listed, Instructions for Use Synvisc-One. Genzyme Corporation. Date of revision: Mar. 3, 2015. Version 1.0. 7 pages.
No Author Listed, JUVÉDERM® VOLUMA™ XC directions for use. 2024. Abbvie. 11 pages. Accessed at: https://www.rxabbvie.com/pdf/juvederm-voluma-xc_dfu.pdf [last accessed Apr. 3, 2024].
No Author Listed, JUVÉDERM® VOLUX™ XC directions for use. 2023. Abbvie. 4 pages. Accessed at: https://www.rxabbvie.com/pdf/juvederm-volux-xc_dfu.pdf. [last accessed Apr. 3, 2024].
No Author Listed, Persica 002 Phase 1b PP353 vs Placebo in the Treatment of Low Back Pain. ClinicalTrials.gov ID NCT04238676. Accessed at: https://www.clinicaltrials.gov/study/NCT04238676. Last updated: Dec. 1, 2023.
No Author Listed, Revolax Material Properties. Fox Pharma. 2024. Accessed: https://foxpharma.co.uk/revolax-dermal-fillers/material-properties/. Last accessed: Apr. 3, 2024.
Peng et al., Treatment of osteomyelitis with teicoplanin-encapsulated biodegradable thermosensitive hydrogel nanoparticles. Biomaterials. Jul. 2010;31(19):5227-36. doi: 10.1016/j.biomaterials.2010.03.027. Epub Apr. 8, 2010.
Romanò et al., Hyaluronic Acid and Its Composites as a Local Antimicrobial/Antiadhesive Barrier. J Bone Jt Infect. Jan. 1, 2017;2(1):63-72. doi: 10.7150/jbji.17705. eCollection 2017.
Telikicherla et al., Accuracy of Needle Placement into the Intra-Articular Space of the Knee in Osteoarthritis Patients for Viscosupplementation. J Clin Diagn Res. Feb. 2016;10(2):RC15-7. doi: 10.7860/JCDR/2016/17127.7275. Epub Feb. 1, 2016.
Wang et al., Intra-discal vancomycin-loaded PLGA microsphere injection for MRSA discitis: an experimental study. Arch Orthop Trauma Surg. Jan. 2011;131(1):111-9. doi: 10.1007/s00402-010-1154-8. Epub Jul. 28, 2010.
Watt et al., Injectability as a function of viscosity and dosing materials for subcutaneous administration. Int J Pharm. Jan. 10, 2019:554:376-386. doi: 10.1016/j.ijpharm.2018.11.012. Epub Nov. 7, 2018.
Wongprasert et al., Evaluating hyaluronic acid dermal fillers: A critique of current characterization methods. Dermatol Ther. Jun. 2022;35(6):e15453. doi: 10.1111/dth.15453. Epub Apr. 5, 2022.

* cited by examiner

ANTIBIOTIC FORMULATIONS FOR LOWER BACK PAIN

CROSS REFERENCE TO RELATED APPLICATIONS

This application is a continuation of U.S. Non-Provisional patent application Ser. No. 17/142,559, filed Jan. 6, 2021, which is a continuation of U.S. Non-Provisional application Ser. No. 16/461,434 filed May 16, 2019, which is 35 U.S.C. § 371 U.S. National Stage Entry of international Application No. PCT/GB2017/053447 filed Nov. 16, 2017, which claims priority to U.S. Provisional Patent Application No. 62/423,112 filed on Nov. 16, 2016; the contents of each of which are incorporated herein by reference in their entirety.

FIELD OF THE INVENTION

The present invention is directed to injectable pharmaceutical compositions comprising thermosensitive hydrogels loaded with antibiotics for relieving low back pain. Particularly, the injectable compositions comprise poloxamer based thermosensitive hydrogels loaded with vancomycin or linezolid.

BACKGROUND OF THE INVENTION

Lower back pain or low back pain (LBP) is common among the general population worldwide. The National Institute of Neurological Disorders and Stroke published in the Low Back Pain Fast Sheet that nearly everyone has low back pain sometime in their life. However, it has been reported that only a small proportion (approximately 20%) of patients with LBP can be diagnosed based on the presence or presentation of a patho-anatomical cause (Waddell, *Spine* 1987, 12: 632-44). Consequently, approximately 80% of LBP patients are classified as "non-specific LBP." Therefore, it is difficult to diagnose and treat lower back pain.

Although LBP relates to different spinal pathologies, it has been shown there is a positive association between Modic changes (bone edema) on MRI and non-specific LBP with a mean odds ratio (OR) of 4.5. A recent systematic review by Jensen et al. showed that the prevalence for any type of Modic changes (e.g., Types I-III) in patients with non-specific LBP was 46% as opposed to 6% in the general population (Jensen et al., *Eur. Spine J.* 2008, 17:1407-1422). These findings are relevant as chronic lower back pain (CLBP) is seldom reliably attributable to specific patho-anatomical causes. Kjaer et al. also observed a strong association between Modic changes and LBP within the past year, particularly for Modic Type 1 changes (MCI), in a sample of 412 persons aged 40 from the general population (Kjaer et al., *Spine* 2005, 30:1173-80). In a study by Albert et al., 166 patients with sciatica (92% from a lumbar disc herniation) were evaluated (*Eur. Spine J.* 2007, 16(7): 977-982). All had a magnetic resonance imaging (MRI) scan in the acute stage and at follow-up 14 months later. At follow-up, 60% of patients with Modic changes suffered from LBP, whereas in the group without Modic changes only 20% had LBP (mean Odds Ratio (OR) of 6.1 (2.9-13.1)) (p<0.0001). The prevalence of Modic changes increased over the 14 months from 25% to 49%.

Modic changes, characterized by edema (or inflammation) in vertebrae, involves disruption and fissuring of the endplate with regions of degeneration (e.g., degenerated intervertebral disc), regeneration, reactive bone formation, endplate edema and vascular granulation of the tissue (Modic et al., *Radiology*, 1988, 166:193-199; and Modic, et al., *Radiology*, 1988, 168:177-186). The pathology of modic changes is hypothesized to be related to infection. A disease model is suggested where disc/endplate damage and the persistence of an inflammatory stimulus create predisposing conditions. The risk to develop Modic changes likely depends on the inflammatory potential of the disc and the capacity of the bone marrow to respond to it. *Proprionibacterium acnes* (*P. acnes*) inside nonpyogenic intervertebral discs has been thought to be one pathogen causing Modic changes and nonspecific low back pain. Stirling et al. found nuclear tissue removed under strict sterile conditions during surgery for lumbar herniated discs to be infected with the low virulent anaerobic organisms, *Proprionibacterium acnes* (*P. acnes*) and *Corynebaterium propinquum* in 53% of the patients (Stirling et al., *Lancet*, 2001, 357:2024-2025). Corsia et al. replicated the Stirling study and evacuated extruded disc material in 30 lumbar disc herniations: 71% were infected, 36% with *Staphylococcus* and 18% with *P. acnes*; and in 30 cervical disc herniations they found 59% were infected, 37% with *P. acnes* (Abstract from Scoliosis Research Society Annual Meeting (2003)). Agarwal et al. cultured material from 52 patients and found 10 (19%) were infected and in 70% of those, *P. acnes* was the sole organism isolated (*Spine J.* 2010, 10: S45-S46). *P. acnes* isolated from a patient associated with Modic change and disc degeneration, when inoculated into the intervertebral discs, can induce disc degeneration and Modic changes (Chen et al., *Biomed Res Int.* 2016: 9612437. doi: 10.1155/2016/9612437. Epub 2016 Jan. 26; and Chen et al., *Int Orthop.* 2016, 40(6):1291-8. doi: 10.1007/s00264-016-3115-5. Epub 2016 Jan. 28). A recent study also demonstrated that within a week of inoculation of *P. acnes*, aseptically isolated from a symptomatic human L4/5 disc with MC1, into rat tail discs, *P. acnes* proliferates and induces inflammatory reaction and degeneration, and cause MC1-like changes in the adjacent bone marrow (Dudli et al., *J Orthop Res.* 2016, 34(8):1447-1455).

It is hypothesized that anaerobic bacteria (like *P. acnes*) from mouth and skin may gain access to the disc. Local inflammation in the adjacent bone may be a secondary effect due to cytokine and propionic acid production, where the infection is in the disc and the Modic change is a "side effect" manifested in the bone.

In a cohort study of 61 immunocompetent patients undergoing surgery for a lumbar disc herniation, nuclear material was removed during surgery under strict sterile conditions and tested for the presence of bacteria. The study revealed that 46% of the patients had infected nuclear material, 84% of these with *P. acnes*. It was also shown that 80% of patients with discs from which anaerobic bacteria were cultured developed new Modic changes in the vertebrae adjacent to the previous disc herniation, compared to only 44% with no identified infection or aerobic bacterial infection (*Eur Spine J.*, 2013, 22(4): 690-696).

Antibiotic therapy may be effective in the treatment of chronic low back pain (disc herniation with Modic Type 1 change). In one background study, 32 patients with CLBP, following a lumbar disc herniation of up to two years duration associated with Modic changes, were treated orally with amoxicillin-clavulanate (500 mg/125 mg) 3 times per day for 90 days. Three patients dropped out due to diarrhea. At the end of treatment and at long-term follow-up (mean 10.8 months), there was both a clinically important and statistically significant (p<0.001) improvement in all outcome measures in patients who completed the treatment (29 out of 32) (*Br. J. Sports Med.* 2008, 42: 969-973). Another study on oral administration of antibiotics (amoxicillin/clavulanic acid) conducted by Albert et al. (*Eur Spine J.* 2013, 22(4): 697-707) showed that patients receiving antibiotic treatment have a 30% reduction of the individual's baseline score and a 2 LBP rating scale points reduction, as well as secondary effectiveness on phenotypic presentations such as leg pain, hours with LBP during the last 4 weeks, constant pain, MRI Modic grading, serum analysis, and days with sick leave, etc. These results provided support for the hypothesis that bacterial infection may play a role in LBP with Modic changes.

Although several non-surgical treatment approaches including intradiscal injections of steroid, anti-TNF-α antibody, antibiotics, and bisphosphonates have demonstrated some short-term efficacy in non-replicated clinical studies in reducing Modic changes and CLBP, none of these approaches is successful and causes controversial results. There is no ideal therapy for Modic changes.

On this background, there is a need in the art for modalities to address the treatment, alleviation, prevention, and/or mitigation of pain found to be coincident with diseases, conditions or disorders of the bones, joints, ligaments and/or tendons, especially those associated with Modic changes or bone edema. The present invention provides pharmaceutical compositions, formulations of antibiotics for relieving, treating and preventing low back pain. Particularly, the present invention provides antibiotic formulations that can increase the delivery of antibiotics to the diseased dics and vertebrae, therefore improve treatment efficacy of Modic changes and LBP.

SUMMARY OF THE INVENTION

The present invention provides pharmaceutical compositions and formulations comprising antibiotics as active ingredients suitable for delivering to the infected spinal sites for treating, preventing, ameliorating, and/or mitigating one or more types of pain, or phenotypic presentations coincident with a clinical condition of the bones, joints, ligaments, or tendons. Kits, packages and methods of using the same are also provided.

In accord with the present invention, compositions and formulations are aqueous solutions in cold temperature and form hydrogels in situ in responding to the warm body temperature. The formulation of the present invention is injectable and thermosensitive.

In some embodiments, pharmaceutical compositions of the present invention comprise an effective amount of at least one antibiotic. The antibiotic may be selected from vancomycin and linezolid. In one embodiment, the antibiotic is vancomycin, including vancomycin salt or free base. Vancomycin may be loaded to the pharmaceutical composition with about 1% to about 50% by weight or by volume of the composition. In some aspects, it may be loaded with about 1% to about 30%, or about 1% to about 20%, or about 2.5% to about 20% by weight or by volume of the composition. In one aspect, the composition may be loaded with 1% (10 mg/ml), 2.5% (25 mg/ml), 5% (50 mg/ml), 10% (100 mg/ml), 20% (200 mg/ml) or 50% (500 mg/ml) vancomycin. In another embodiment, the antibiotic is linezolid. Linezolid may be loaded to the pharmaceutical composition with about 1% to 50% by weight or by volume of the composition. In some aspects, it may be loaded with about 1% to about 20%, or about 2.5% to about 20% by weight or by volume of the composition. In one aspect, the composition may comprise about 1% (10 mg/ml), 2.5% (25 mg/ml), 5% (50 mg/ml), 10% (100 mg/ml), 20% (200 mg/ml) or 50% (500 mg/ml) linezolid.

In some embodiments, pharmaceutical compositions of the present invention comprise at least one pharmaceutically acceptable biodegradable and biocompatible polymer which forms hydrogel in responding to the temperature increase. In some aspects, the thermosensitive polymers are Poloxamer 407. Pharmaceutical compositions of the present invention may comprise Poloxamer 407 with about 5% to about 20% by weight or by volume of the composition. Preferably it may comprise Poloxamer 407 with about 10% to about 20% by weight or by volume of the composition. Pharmaceutical compositions of the present invention may further comprise another poloxamer, such as poloxamer 188, with about 5% to about 20% by weight or by volume of the composition.

In some embodiments, pharmaceutical compositions of the present invention may further comprise one or more excipient to increase solubility of linezolid. In some aspects, the excipient is a cyclodextrin. The composition may comprise about 15% to about 40% of cyclodextrin by weight or by volume of the composition. In one example, it may comprise about 20%, 25% or 30% of cyclodextrin.

In some embodiments, pharmaceutical compositions of the present invention may be prepared as vehicles to facilitate injection. In one aspect, the vehicle facilitating injection comprises a radio-opaque dye, e.g. Iohexal, Iopamidol, Ioxilan, Iopromide, Iodixanol, Diatrizoate, Metrizoate, or Ioxaglate. An injectable vehicle comprising the present composition may be administered locally at or near a bone, a joint, a ligament, or a tendon, such as the vertebra.

In some embodiments, compositions may form injectable thermosensitive hydrogels for locally delivering antibiotics. The optimal formulations provide effective amount of antibiotics for the local treatment of lower back pain.

Formulations of the present invention may be applied to a subject in need in the lumbar intervertebral disc and/or the adjacent vertebrae, ligaments, muscles and joints, and the application is carried out by open surgery or by injection or by means of a microsurgical or percutaneous technique.

In some embodiments, the present invention provides a kit comprising the present compositions, vehicles and a syringe and/or needle for administering the sterile injectable formulation of the present invention.

DETAILED DESCRIPTION OF THE INVENTION

Figure 1:
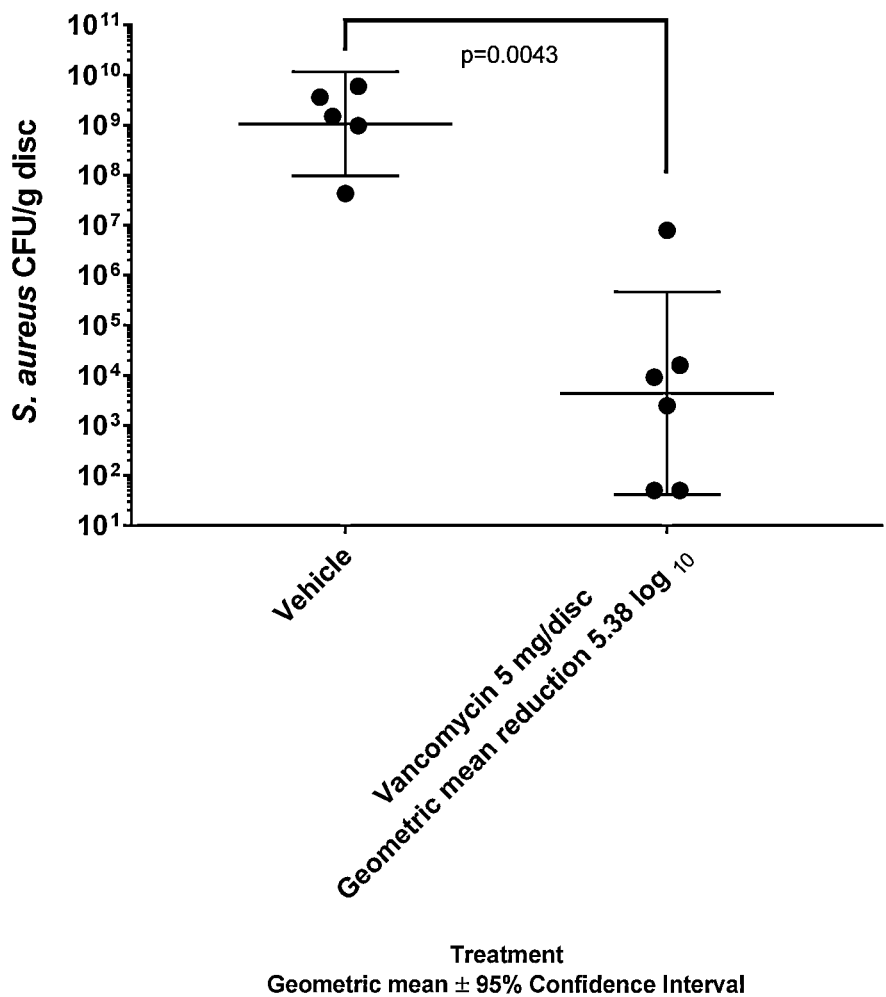
FIG. 1 shows *S. aurens* proliferation after prophylactic treatment with vancomycin.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

The present invention relates to local and controlled delivery of an effective amount of active medicine to a diseased site/sites, or areas closely next to the site(s) that need to be treated. Active drugs are formulated in thermosensitive polymers that form degradable gels in response to the temperature changes. These thermosensitive carriers, which are aqueous solutions at cold or room temperature for a period of time that is long enough for administration to the target site(s), form a gel in situ at body temperature and release the carried active drugs to the target site(s). Such formulations and administration can increase the amount of active drugs at the target sites.

The present invention is based on discoveries in human studies that lower back pain is often associated with Modic change and disc herniation in which bacterial infection is observed. In accordance, pharmaceutical compositions, formulations and methods are provided for treating, preventing, ameliorating, and/or mitigating one or more types of pain or phenotypic presentation found to be coincident with diseases, conditions or disorders of the bones, joints, ligaments and/or tendons, especially where there is an association with Modic changes or bone edema caused by bacteria infection. In particular, formulations that can be readily injected to sites near the infected sites and provide treatment for pain in the patient is also provided in the present invention.

Previous studies have demonstrated that vancomycin can be dispersed in poloxamer matrices for controlled and prolonged release of vancomycin. The combination does not affect the rheological characteristics of the poloxamer matrices, or the antibiotic activity of vancomycin (Veyries et al., *Int. J. Pharm.*, 1999, 192(2): 183-193.) These previous investigation indicates that thermosensitive polymers such as poloxamers may be useful as a drug delivery vehicle.

Kalorewicz et al., (*Polim. Med*, 2011, 41(4) 3-15) in an in vitro study showed that vancomycin dispersed in a 25% pluronic F-127 solution, can be converted into gel in responding to temperature increase. Vancomycin is released from the hydrogel. Vancomycin has been formulated with poloxamer 407 for locally delivering to the MRSA (methicillin resistant *Staphylococcus aureus*) infected ear. The sustained local delivery of vancomycin from the gel matrix effectively inhibits the MRSA growth and completely cures the otitis media caused by MRSA infection in a preclinical model (Lee et al., *J Control Release*, 2004, 96(1): 1-7).

According to the present invention, compositions, formulations and methods are described which are useful in treating, alleviating, preventing, or mitigating pain or phenotypic presentations coincident with a clinical condition. Types of pain may include, but are not limited to, acute pain, sub-acute pain, chronic or constant pain, local pain, radicular pain, referred pain, somatic pain, radiating pain, neuropathic pain, inflammatory pain, and pain of mixed or non-specific origin. Pain may present in various parts of the body including the limbs, muscles, skin, joints, or deep tissues or organs. As such, pain may be present in the arms, legs, hands, feet, neck, joints, pelvis, or spine (including the cervical, thoracic, lumbar or sacral spine).

Phenotypic presentations, defined as any outward manifestation, whether perceived or experienced by a subject, may include, but are not limited to any type of pain generally, disturbed sleep at night due to pain, pain during the Valsalva maneuver, pain during active flexion of the lumbar spine, pain during active extension of the lumbar spine, positive Cranial Compression test, pain during Springing test, difficulty to turn over in bed, difficulty to get out of a chair, difficulty to get on stairs, difficulty to bend or kneel down, and difficulty to stand or walk for a long time. A phenotypic presentation may be of any kind of pain, be accompanied by pain, or be the causal agent (or result) of pain.

Diseases, conditions or disorders of the bones, joints, ligaments and/or tendons that are coincident with pain include, but are not limited to: Modic changes, bone edema, lumbar disc herniation, tendonitis, tendon rupture, ligament inflammation, ligament rupture, symphysiolysis, pelvic girdle syndrome, and Scheuermann's disease.

The pain or phenotypic presentation may be (1) caused by the disease, condition or disorder, (2) occur at the same time as the disease, condition or disorder, (3) present at or close to the site of the disease condition or disorder, or (4) any combination of the foregoing. Pain, if present, may be measured with disease-specific disability Roland Morris Questionnaire (RMDQ), lumbar back pain rating scale (LB-PRS), hours with low back pain during the last 4 weeks, SF-36 health questionnaire, EQ-5D health questionnaire, days with sick leave due to pain, and bothersomeness reported by patient. The RMDQ, LBPRS, SF 36 and EQ-5D health questionnaires are all well-recognized and widely-utilized rating systems. Examples of diseases that cause lower back pain include arthritis, Diffuse Idiopathic Skeletal Hyperostosis (DISH or Forestier's Disease), sciatica, degenerative disc disease, lumbar spinal stenosis, spondylolisthesis, herniated disc, scoliosis, radiculopathy, joint dysfunction, coccydynia, endometriosis and osteoporosis.

I. Compositions of the Present Invention

Pharmaceutical compositions and formulations of the present invention comprise antibiotic components in combination with one or more pharmaceutically-acceptable carriers or excipients to treat, prevent, ameliorate, or mitigate pain. Pharmaceutical compositions and formulations may optionally comprise one or more additional active substances, e.g. therapeutically and/or prophylactically active substances.

In some embodiments, compositions are administered to humans, human patients or subjects. For the purposes of the present disclosure, the phrase "active ingredient" generally refers to an antibiotic or a combination of antibiotics to be delivered as described herein.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The pharmaceutical composition of the present invention may comprise a therapeutically effective amount of antibiotic formulated in a thermosensitive hydrogel and at least one pharmaceutically acceptable carrier or excipient. Relative amounts of the active ingredient (i.e. antibiotic), the pharmaceutically-acceptable excipient, and/or any additional ingredients in a pharmaceutical composition in accordance with the invention will vary, depending upon the identity, size, and/or condition of the subject treated and further depending upon the route by which the composition is to be administered. By way of example, the pharmaceutical composition may comprise between 0.1% and 100%, e.g., between 0.5% and 50%, between 1 and 30%, between 5 and 60%, between 10 and 80%, at least 90%, at least 80%, at least 70%, at least 60%, or at least 50% active ingredient in the composition.

A pharmaceutical composition in accordance with the invention may be injectable. The injectable pharmaceutical compositions are formulated to be injected to an intervertebral disc, intervertebral space, intra-articular space, ligament, tendon, tendon and bone junction, or site adjacent to bone edema. The injectional formulations comprise at least one polymer which forms a solution at cold temperature but gels at body temperature. The thermosensitive hydrogels carry the loaded antibiotics to the injected site, where antibiotic is effective against infections. The gelling formulation of the present invention may stay long enough in the injected place for the antibiotic to diffuse into the disc tissue. This feature is particularly beneficial in damaged discs where a quite fluid administration might quickly leak out of the disc when the injection needle is withdrawn.

In some examples, the compositions may comprise at least another anti-inflammatory agent or another anti-infection agent. In particle, the injectable compositions comprise poloxamer based thermosensitive hydrogels loaded with vancomycin or linezolid.

In some embodiments, an injectable pharmaceutical composition in accordance with the invention may comprise a contrast agent. The contrast agent may be an ionic agent or a non-ionic agent, including but not limited to Iohexol, Iopamidol, Iopromide, Ioxilan, Iodixanol, Ioversol, Diatrizoate, Metrizoate, Iothalamate and Ioxaglate.

In some embodiments, an injectable pharmaceutical composition of the present invention may further comprise at least one pharmaceutically acceptable carrier or excipient. In some aspects, the excipient may be a cyclodextrin.

Active Ingredients

As described in the background, lower back pain is often closely related to Modic changes following lumbar disc herniation. Since anaerobic bacteria are often observed in the nuclear tissues of lumbar herniated discs, pharmaceutical compositions of the present invention comprising at least one antibiotic as an active ingredient may be administered to patients with lower back pain or to patients at risk of developing lower back pain. In some embodiments, the subject to whom the therapeutic agent is administered suffers from or is at risk of developing pain at or near a bone, a joint, a ligament, or a tendon.

The active agents of the invention include any antibiotic that kills or inhibits one or more target bacteria. Representative classes of antibiotics suitable for use in the pharmaceutical compositions of the present invention include beta-lactams (comprising penicillins, cephalosporins, carbapenems, monobactams, and others), oxazolidinones, aminoglycosides, glycopeptides, lipopeptides, and glycylcyclines. Further representative antibiotics suitable for use in the pharmaceutical composition of the present invention comprise vancomycin, linezolid, erythromycin, rifampicin, ciprofloxacin, fusidic acid, tetracycline, clindamycin, doxycycline, minocycline, imipenem, levofloxacin, gatifloxacin, moxifloxacin, oxytetracycline, chloramphenicol, cefotaxime, teicoplanin, ofloxacin, metronidazole, fosfomycin, piperacillin, meropenem, torezolid, radezolid, tobramycin, retapamulin, daptomycin, televancin, ceftaroline, ceftobiprole, ortitavancin, dalbavancin, solithromycin or combinations thereof.

Selection of active agents may depend on the bacterial pathogens isolated from modic discs. The bacterial pathogens most frequently isolated form modic discs are *Staphylococcus* spp. and *P. acnes*. Antibiotics resistances vary in different populations and territories worldwide. To have a robust and widely effective therapy, coverage of common resistances would be preferred with *P. acnes* and *Staphylococcus*, or with *P. acnes* only as a minimum. Preferably, antibiotics that are effective against current clinical isolates from any infection site may be selected as active agents of the present compositions and formulations, given the resistance profiles of pathogens isolated at the site of infection associated with Modic changes.

For example, pharmaceutical formulations of the present invention may comprise active agents for treating both *Staphylococcus* spp. and *P. acnes* which are the bacterial pathogens most frequently isolated form modic discs. In some aspects, pharmaceutical formulations of the present invention may comprise at least one antibiotic for the treatment of the *P. acnes* infection that causes the majority of the investigated infection, about 38% of Modic Type 1 patients. Evidence from prior treatment with a number of potential antibacterial therapies for *P. acnes* and *Staphylococcus* spp. respectively identified several antibiotics that are effective again at least one of the pathogens. Exemplary antibiotics for *P. acnes* include Chloramphenicol, Linezolid, Retapamulin, Streptomycin, Vancomycin, Teicoplanin, Daptomycin, Dalbavancin and Rifampicin. Exemplary antibiotics for *Staphylococcus* include Linezolid, Retapamulin, Vancomycin, Teicoplanin, Daptomycin, Televancin, Dalbavancin, Rifampicin and Netilmicin.

In accordance with the present invention, antibiotics that are effective against both *P. acnes* and Staphylococci may be selected as active agents of the present compositions and formulations. In some embodiments, a combination of the antibiotics that are effective against both *P. acnes* and Staphylococci may be selected. Such antibiotics may be selected from Linezolid, Retapamulin, Vancomycin, Teicoplanin, Daptomycin, Televancin, Dalbavancin and Rifampicin. Preferably, such antibiotics may be linezolid and vancomycin.

In one embodiment, the antibiotic is vancomycin. Vancomycin is a hydrophilic glycopeptide against Gram-positive bacteria including *Staphylococcus* and *Enterococcus* species. It is commonly used due to its effectiveness in treating serious gram-positive infections (Olsson et al., APMIS. 2012, 120(10):778-785). The pharmacokinetic parameters for vancomycin and serum vancomycin concentration—time profile from a variety of patient population have been well characterized. It is expected that targeting the vancomycin concentrations within a relatively narrow range can minimize toxicity yet still achieve therapeutic success. It is recommended by the Infectious Diseases Society of America, that the area under the concentration-time curve (AUC): minimum inhibitory concentration (MIC) ratio is the most useful pharmacodynamic parameter to predict vancomycin effectiveness to eradicate *S. aureus* (Rybak et al., American J. Health system Pharmacy, 2009, 66(1): 82-98). A dosage strategy to increase the concentration of vancomycin and to reduce its toxicity may potentiate the effectiveness in eradicating bacteria and treating infections. It is also shown that vancomycin can be safely used against infection for example, for spine surgery (Gans et al., Spine (Phila Pa. 1976). 2013, 38(19):1703-1707; and Sweet et al., Spine (Phila Pa. 1976). 2011, 36(24):2084-2088). In the context of the present invention, the effectiveness of vancomycin against infection causing Modic Change relies on achieving adequate exposure of vancomycin to the infected area of the bone, joint, ligament and tendon.

In another embodiment, the antibiotic is linezolid. Linezolid is the first clinically used oxazolidinone against most Gram-positive bacteria that cause disease, including streptococci, vancomycin-resistant enterococci (VRE), and methicillin-resistant *Staphylococcus aureus* (MRSA) (Gaudin et al., Eur J Clin Microbiol Infect Dis. 2013, 32(2):195-198). It has been used successfully for the treatment of patients with endocarditis and bacteraemia, osteomyelitis, joint infections and tuberculosis and it is often used for treatment of complicated infections when other therapies have failed (Gautier et al., JM. J Biomater Appl. 2012, 26(7):811-828; Tsiolis et al., Surg Infect (Larchmt). 2011, 12(2): 131-135). Long-term use (e.g., more than 2 weeks) of linezolid could cause serious side effect (Falagas et al., Int. J Antimic Agents, 2007, 29(3): 233-239). Linezolid is well absorbed, with a bioavailability of approximately 100% in healthy volunteers. Linezolid can penetrate to tissues relatively fast to reach its MIC at 4 mg/L. It can also penetrate to intervertebral discs and surrounding tissues (Komatsu et al., Eur Spine J. 2010, 19(12): 2149-2155). Higher success rates for linezolid may occur at AUC: MIC values of 80-120 and when concentrations remain above the MIC for the entire dosing interval (reviewed by Dryden, J. Antimicrob. Chemother. 2011, 66 (suppl 4): iv7-iv15).

An effective amount of the compositions of the invention is provided based, at least in part, on the target bacteria, means of administration, and other determinants. In general, an effective amount of the composition provides efficient killing or inhibition of target bacteria and reduces pain or the risk of developing pain in a patient.

In some embodiments, an effective dosage level of the antibiotic of the invention is above the minimum inhibitory concentration (MIC) of the target bacteria.

In certain embodiments, target bacteria are anaerobic bacteria, such as *P. acnes, Corynebacterium propinquum*, or those of the genus *Staphylococcus*.

In certain embodiments are provided combination therapeutics containing one or more antibiotics. The antibiotics may be vancomycin and linezolid.

1. Companion Drugs

Companion (or drugs given in combination) drugs may be administered along with the active ingredients of the present invention. In certain embodiments, an anti-inflammatory drug is also administered, such as aspirin, ibuprofen, ketoprofen, naproxen, cefacoxib, rofecoxib, parecoxib, celecoxib, valdecoxib, and indomethacin. In certain embodiments, a pain relieving medication is also administered, such as acetaminophen, morphine, oxycodone, and codeine. Companion drugs may also include over-the-counter pain relieving patches, drugs and/or ointments.

Contrast Agents

Though previous research indicates the poloxamer entrapped antibiotics including vancomycin and linezolid can be used for controlled and sustained release of antibiotics to increase its effectiveness in inhibiting bacterial proliferation (Veyries et al., Int. J. Pharm., 1999, 192(2): 183-193; Veyries et al., Antimicrob Agents Chemother., 2000, 44(4):1093-1096; Kalorewicz et al., Polim. Med, 2011, 41(4) 3-15; and Lee et al., J Control Release, 2004, 96(1): 1-7), none of these previous studies investigate the effect of addition of other pharmaceutical carriers such as contrast agents. Experiments conducted in the present invention indicated that the addition to the contrast agent Iohexol to formulations comprising vancomycin or linezolid increases the radiographic visibility of the composition for monitoring its delivery to the diseased sites.

In accordance with the present invention, the antibiotic composition of the present invention may comprise a radiocontrast agent. The addition of a radiocontrast agent in the present antibiotic formulations will assist a clinic practitioner (like a physician) to see the product being administered, and monitor the condition of the disc being administered using fluoroscopy. This real-time information can help the practitioner to decide when to stop injection when the dics is full and is starting to leak. The contrast agent may be an ionic agent selecting from Diatrizoate, Metrizoate, and Ioxaglate or the like, or a non-ionic contrast agent selecting from Iohexol, Iopamidol, Iopromide, Iodixanol, Ioxilan, Ioversol, or the like. Preferably, the contrast agent is a non-ionic agent.

II. Pharmaceutical Formulations

The present invention provides pharmaceutical formulations for administering to the antibiotic compositions as discussed herein to a diseased site (or sites) for treating, preventing, ameliorating, or mitigating pain and simultaneously eliminating bacterial infection in a cervical, thoracic, lumbar or sacral vertebra. The formulations may comprise antibiotic compositions and complexes in combination with one or more pharmaceutically-acceptable carriers or excipients. General considerations in the formulation and/or manufacture of pharmaceutical agents may be found, for example, in Remington: The Science and Practice of Pharmacy 21st ed., Lippincott Williams & Wilkins, 2005 (the contents of which are incorporated herein by reference).

Antibiotics such as vancomycin and/or linezolid may be entrapped into a delivery vehicle for administration to a subject in need. In addition, the formulation may increase the stability and solubility of antibiotics. The delivery vehicle may be suitable for injection. For example, it may be an aqueous solution, a low viscous solution or a reversible thermogel. The vehicle preferably is a biodegradable and biocompatible carrier. As used herein, the terms "biodegradable" and "bioabsorbable" are used interchangeably. The biodegradation or bioabsorbance in the context of the present invention refers to the degradation, disassembly, digestion or disappearance of the delivery materials after releasing formulated therapeutically active ingredients, in the biological environment through the action of living organisms and most notably at physiological pH and temperature. Specific reactions include but are not limited to chemical or enzymatic degradation.

The biodegradable carriers used for formulating antibiotics and compositions of the present invention may be hyaluronic acid (HA), thermosensitive hydrogels and other polymeric biomaterials.

Thermosensitive Hydrogels

Thermosensitive hydrogels biomaterials used in drug delivery. Especially injectable thermosensitive hydrogels with solution-gel transition temperature around physiological temperature are useful. The thermosensitive hydrogels are liquid at low temperature (e.g. at room temperature). By in vivo injection, the hydrogels formed non-flowing/stiff gel at body temperature. The temperature of phase transition from solution to gel is referred to as lower critical solution temperature (LCST). Over several hours or days, the gels break down. Varying the concentrations of components in the formulation can allow fine tuning of the properties, such as LCST or rate of degradation, of the gels. Upon incorporation of pharmaceutical agents, the hydrogel systems could act as sustained drug release depot in situ. Injectable thermosensitive hydrogel systems have a number of advantages, including simplicity of drug formulation, protective environment for drugs, prolonged and localized drug delivery, and ease of application.

Thermosensitive hydrogel may be made up by synthetic polymers, natural polymers or a combination thereof. The pharmaceutical agents (e.g. antibiotics) and appropriate carriers may be mixed with the precursor polymer solutions in vitro prior to gelation and the drug-loaded hydrogel can form in situ after in vivo administration.

In some embodiments, the thermosensitive hydrogel may be formed by synthetic polymers. The synthetic polymers may include, but are not limited to, poly(ethylene oxide)-poly(propylene oxide)-poly(ethylene oxide) (PEO-PPO-PPO) triblock copolymers (also known as Poloxamers® or Pluronics®) and derivatives thereof, poly (N-isopropylacrylamide) based (PNIPAAM) copolymers and derivatives thereof, poly(organophosphazene), and poly(ethylene glycol) (PEG)/biodegradable polyester copolymers.

Poloxamers® or Pluronics® are FDA-approved thermosensitive synthetic polymers. Poloxamers are nonionic triblock copolymers composed of a central hydrophobic chain of polyoxypropylene (poly(propylene oxide)) flanked by two hydrophilic chains of polyoxyethylene (poly(ethylene oxide)). Biocompatible Poloxamers have been widely used for drug delivery and tissue engineering. Poloxamer-based hydrogels allow reversible gelation under certain physiological temperature and pH by adjusting the composition of PEO and PPO, and the overall molecular weight and concentration. The Poloxamers that have been used for drug delivery include, but are not limited to, Poloxamer® 188 (Pluronic® F-68, FLOCOR or RheothRx), Poloxamer® 237 (Pluronic® F87), Poloxamer® 238 (Pluronic® F-88), Pluronic® F-98, Poloxamer®124 (Pluronic® L-44), Poloxamer®184 (L-64), Poloxamer® 338 (Pluronic® F-108), Poloxamer® 401 (Pluronic® L-121) and Poloxamer® 407 (Pluronic® F-127). The physicochemical characteristics and gel-forming properties of some selected Poloxamers can be found in Table 1 from U.S. Pat. No. 5,702,717; the contents of which are herein incorporated by reference in its entirety.

Poloxamer® 407 (Pluronic® F-127) is one of the least toxic of the block copolymers and has been used extensively as drug delivery systems. At a concentration of pure 20% (w/w), Poloxamer® 407 is liquid in an aqueous solution at or below room temperature (~25° C.), but forms a soft gel at body temperature (37° C.). Poloxamer® 407 consists by weight of approximately 70% PEO and 30% PPO with an average molecular weight of 11500. Like other Poloxamers, Poloxamer® 407 exhibits thermoreversible gelation behavior. Poloxamer® 407 has been employed for the delivery of many drugs, proteins and genes, as reviewed in Gong et al. (*Curr. Med. Chem.* 2013, 20, 79-94; the contents of which are herein incorporated by reference in their entirety). In most cases, drug loaded Poloxamer® 407 hydrogel allows sustained release of the drug over several hours up to days.

Poloxamer 188 is a nonionic linear copolymer having an average molecular weight of 8400 Daltons, and was approved by the FDA nearly 50 years ago as a therapeutic reagent to reduce viscosity in the blood before transfusions. The surfactant properties of poloxamer 188 make the copolymer extremely useful in pharmaceutical applications.

Poly NIPAAM (PNIPAAM) is another well studied thermosensitive polymer material. PNIPAAM has mechanical and gelation properties suitable for injectable hydrogens. PNIPAAM is soluble below 32° C. and precipitates quickly at or above 32° C. under physiological conditions. The LCST of PNIPAAM can be modulated by grafting with other monomers. For example, copolymerization of PNIPAAM with a more hydrophilic monomer leads to an elevated LCST, while copolymerization of PNIPAAM with a more hydrophobic monomer leads to a lower LCST.

PEG/biodegradable polyester copolymers are copolymers of hydrophilic biocompatible PEG with biodegradable biocompatible aliphatic polyesters. The PEG/polyester copolymers described herein include, but are not limited to, PEG/polylactide (PEG/PLA) block copolymers, PEG/poly (lactide-co-glycolide) (PEG/PLGA) block copolymers, PEG/poly(ε-caprolactone) (PEG/PCL) block copolymers, PEG/poly(ε-caprolactone-co-lactide) (PEG/PCLA) copolymers, and PEG/poly[(R)-3-hydroxubutyrate] (PEG/PHB) copolymer. Synthesis and properties of some PEG/polyester copolymer based hydrogels have been reviewed in Nguyen and Lee (*Macromol. Biosci.* 2010, 10, 563-579) and Gong et al. (*Curr. Med. Chem.* 2013, 20, 79-94; the contents of each of which are herein incorporated by reference in their entirety. As a non-limiting example, the PEG/polyester copolymers may be any thermosensitive biodegradable polymer based on poly(ether-ester) block copolymers described in U.S. Pat. No. 5,702,717; the contents of which are herein incorporated by reference in their entirety.

In some embodiments, the thermosensitive hydrogel may be formed by natural polymers. Many natural polymers exhibit thermos-sensitivity, biocompatibility and biodegradation. However, some natural polymers lack intrinsic thermosensitive properties or have thermosensitivity outside the physiological temperature. In these cases, modifications are necessary to improve the thermoresponsive gelation behavior of the polymer. The natural polymers that may be used to form thermosensitive hydrogels include, but are not limited to, chitosan and related derivatives, methylcellulose, alginate, hyaluronic acid, dextran, and xyloglucan.

Chitosan, a linear polysaccharide derived from partial deacetylation of chitin, is an FDA approved biomaterial widely used in drug delivery. As a natural polymer, chitosan has advantages such as biodegradability, biocompatibility, non-toxicity, and bioadhesive properties. However, chitosan does not exhibit thermosensitive gelation behavior and requires engineering with other thermosensitive materials to acquire thermosensitivity. As non-limiting examples, the thermosensitive gelling polymers derived from chitosan include chitosan/β-glycerol phosphate (GP), PEG-g-chitosan, Pluronic-chitosan copolymer, chitosan-g-NIPAAM, and N-acetylation of glycol chitosan.

Methylcellulose is a derivative of the naturally occurring polysaccharide cellulose. It is hydrophilic and water soluble at ambient temperature, but turns hydrophobic and thermosensitive at 60-80° C. Since this is beyond physiological temperature, modifications are needed to reduce the transition temperature to physiological temperature. As a non-limiting example, methylcellulose may be grafted to a synthetic polymer such as NIPAAM. As another non-limiting example, methylcellulose may be blended with another natural polymer such as chitosan.

In other embodiments, polymers that may be used to develop injectable thermosensitive hydrogels may also include, an HA polymer with a copolymer of polyethylene oxide (PEO)/polypropylene oxide (PPO) as disclosed in U.S. Pat. No. 9,364,545; amphiphilic triblock copolymers composed of two hydrophobic blocks linked by a linear poly(ethylene glycol) block (see, e.g., U.S. Pat. No. 9,364,544); thermosensitive polyphosphazene hydrogels as discussed in U.S. Pat. No. 7,259,225; thermosensitive pluronic polymer derivative hydrogel (See, e.g., US Patent publication NO.: US2010/0098762); glycol chitin/progesterone as disclosed in PCT patent application publication NO. WO2015/073066; and other polymers disclosed in PCT Patent Publication NOs.: WO2001/04735, WO2007/083875, WO2015/048988, and WO2015/012899, and US Patent publication NOs.: US2013/0230495, US2015/0025106, US2016/0030581 and US2016/0243026; the contents of each of which are incorporated herein by reference in their entirety.

Other Carriers and Excipients

Pharmaceutical formulations may additionally comprise a pharmaceutically-acceptable excipient, which, as used herein, includes, but are not limited to, any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Various excipients for formulating pharmaceutical compositions and techniques for preparing the composition are known in the art (see Remington: The Science and Practice of Pharmacy, 21st Edition, A. R. Gennaro, Lippincott, Williams & Wilkins, Baltimore, MD, 2006; incorporated herein by reference). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition.

In some embodiments, a pharmaceutically-acceptable excipient may be at least 95%, at least 96%, at least 97%, at least 98%, at least 99%, or 100% pure. In some embodiments, an excipient may be approved for use for humans and for veterinary use. In some embodiments, an excipient may be approved by United States Food and Drug Administration. In some embodiments, an excipient may be of pharmaceutical grade. In some embodiments, an excipient may meet the standards of the United States Pharmacopoeia (USP), the European Pharmacopoeia (EP), the British Pharmacopoeia, and/or the International Pharmacopoeia.

Pharmaceutically-acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical formulations. The composition may also include excipients such as cocoa butter and suppository waxes, coloring agents, coating agents, sweetening, flavoring, and/or perfuming agents.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, corn-starch, powdered sugar, etc., and/or combinations thereof.

The present disclosure also includes pharmaceutically acceptable salts of the compounds described herein.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM®), sodium lauryl sulfate, quaternary ammonium compounds, etc., and/or combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays, long chain amino acid derivatives, high molecular weight alcohols, carbomers, carrageenan, cellulosic derivatives, sorbitan fatty acid esters (e.g., TWEEN 20), polyoxyethylene esters (e.g. polyoxyethylene monostearate [MYRJ®45], polyoxyethylene hydrogenated castor oil, polyethoxylated castor oil, polyoxymethylene stearate, and SOLUTOL®), sucrose fatty acid esters, polyethylene glycol fatty acid esters (e.g. CREMOPHOR®), polyoxyethylene ethers, (e.g. polyoxyethylene lauryl ether [BRIJ®30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, PLUORINC®F 68, POLOXAMER®188, POLOXAMER®407, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol,); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (VEEGUM®), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include, but are not limited to, antioxidants, chelating agents, antimicrobial preservatives, antifungal preservatives, alcohol preservatives, acidic preservatives, and/or other preservatives. Exemplary antioxidants include, but are not limited to, alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Exemplary alcohol preservatives include, but are not limited to, ethanol, polyethylene glycol, phenol, phenolic compounds, bisphenol, chlorobutanol, hydroxybenzoate, and/or phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and/or phytic acid. Other preservatives include, but are not limited to, tocopherol, tocopherol acetate, deteroxime mesylate, cetrimide, butylated hydroxyanisol (BHA), butylated hydroxytoluene (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT PLUS®, PHENONIP®, methylparaben, GERMALL®115, GERMABEN®II, NEOLONE™, KATHON™, and/or EUXYL®.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, d-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and/or combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and/or combinations thereof.

Excipients such as cocoa butter and suppository waxes, coloring agents, coating agents, sweetening, flavoring, and/or perfuming agents can be present in the composition, according to the judgment of the formulator.

Formulations

Formulations of the pharmaceutical compositions described herein may be prepared by any method known or hereafter developed in the art of pharmacology. In general, such preparatory methods include the step of associating the active ingredient with a conjugate and/or one or more other accessory ingredients.

The antibiotics of the present invention may be formulated for delivering to anatomical structures of a subject. Structures may include any structure of the body including but not limited to joints, intra-articular spaces, inter-vertebral discs, intervertebral spaces, epidural space, facet joints, spinal ganglion, ligament and other spinal compartments. In one aspect, the antibiotics and compositions of the present invention are formulated for delivering into inter-vertebral discs. In another aspect, the antibiotics and compositions of the present invention are formulated for delivering into the inter-vertebral disc space.

Compositions, formulations of the present invention may be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient may generally be equal to the dosage of the active ingredient which would be administered to a subject and/or a convenient fraction of such a dosage including, but not limited to, one-half or one-third of such a dosage.

In some embodiments, formulations of the present invention may be an isotonic aqueous solution which is suitable for injection in the human or animal body. The injectable solution has an osmotic pressure comparable or at least compatible with the osmotic pressure of human, in particular the osmotic pressure in the spine.

In some embodiments, antibiotics, compositions of the present invention may be formulated using biocompatible and biodegradable polymers and other compounds. The formulations may be nanoparticles and other injectable forms such as aqueous solutions, viscous solutions, thermosensitive hydrogels and suspensions. In one aspect, the formulations are thermosensitive hydrogels. The polymer carriers may be solubilized in aqueous solutions at cold temperature with preferable concentrations to achieve thermogelation of formation at body temperature after administration to a subject. The aqueous preparations comprising the antibiotics and pharmaceutical compositions are injectable at cold temperature. The optimal concentration of polymers may be adjusted to form thermogels after addition of therapeutically active agents to a polymer solution. The therapeutically active agents may be dissolved, emulsified, or suspended (e.g. microcrystals) in the polymer solution.

One issue to develop a desired thermosensitive hydrogel for delivery of therapeutic drugs is the injectability or syringeability problem which represents a critical issue for clinical usage. High viscosity and premature gelation inside the needle are the two aspects of such injectability problem. The present invention investigated different combinations of the compositions and optimized formulations suitable for use in human and other animals.

The pharmaceutical formulations of the present invention comprise a thermosensitive hydrogel loaded with an effective amount of antibiotics and at least one pharmaceutically acceptably excipient.

In some embodiments, the pharmaceutical formulations may comprise antibiotics as therapeutically active agents. The antibiotics may include, but not are limited to, beta-lactams, oxazolidinones, aminoglycosides, glycopeptides, lipopeptides, glycylcyclines, vancomycin, linezolid, erythromycin, rifampicin, ciprofloxacin, fusidic acid, tetracycline, clindamycin, doxycycline, minocycline, imipenem, levofloxacin, gatifloxacin, moxifloxacin, oxytetracycline, chloramphenicol, cefotaxime, teicoplanin, ofloxacin, metronidazole, fosfomycin, piperacillin, meropenem, torezolid, radezolid, tobramycin, retapamulin, daptomycin, televancin, ceftaroline, ceftobiprole, ortitavancin, dalbavancin, teicoplanin, quinupristin/dalfopristin, daptomycin, ceftobiprole, dalbavancin, telavancin, oritavancin, solithromycin and iclaprim, or the combination thereof. In some aspects, the antibiotic is vancomycin or linezolid.

In one embodiment, the pharmaceutical formulations of the present invention comprise vancomycin at a concentration ranging from about 1% to about 50% by weight or by volume of the composition. In one aspect, it may be loaded with about 1% to about 30%, or about 1% to about 20%, or about 2.5% to about 20% vancomycin by weight or by volume of the composition. For example, it may comprise about 1% (10 mg/ml), 2.5% (25 mg/ml), 5% (50 mg/ml), 10% (100 mg/ml), 15% (150 mg/ml), 20% (200 mg/ml), 25% (250 mg/ml), 30% (300 mg/ml), 40% (400 mg/ml), or 50% (500 mg/ml), vancomycin by weight of the composition.

In some aspects, the formulations comprising vancomycin may be aqueous solution which is ready for administration. In other aspects, the formulations comprising poloxamer vehicle and lyophilized vancomycin which are to be mixed for resuspension prior to use.

In another embodiment, the pharmaceutical formulations of the present invention comprise linezolid at a concentration ranging from about 1% to 50% by weight or by volume of the composition. In some aspects, it may be loaded with about 1% to about 20%, or about 2.5% to about 20% by weight or by volume of the composition. In one aspect, the composition may comprise about 1% (10 mg/ml), 2.5% (25 mg/ml), 5% (50 mg/ml), 10% (100 mg/ml), 20% (200 mg/ml), 30% (300 mg/ml), or 50% (500 mg/ml) linezolid by weight or by volume of the composition.

In some aspects, the formulations comprising linezolid may be a suspension in poloxamer vehicle. In other aspects, the formulations comprising linezolid may be viscous solution. In other embodiments, linezolid may be solubilized using cyclodewtrins. The solubilized linezolid may be formulated to an aqueous solution.

In some embodiments, the pharmaceutical formulations comprise thermosensitive hydrogels composed of poloxamer polymers in an amount of between about 5% to about 80% by weight or by volume of the composition, or about 10% to about 50% by weight, or by volume of the composition, preferably about 10% to about 30% by weight, or by volume of the composition. In some aspects, the pharmaceutical compositions comprise, by weight, or by volume of the composition, about 5%, at about 8%, at about 10%, at about 11%, at about 12%, at about 13%, at about 14%, at about 15%, at about 16%, at about 17%, at about 18%, at about 19%, at about 20%, at about 25%, at about 30%, at about 35%, at about 40%, at about 45%, at about 50%, at about 55%, at about 60%, at about 70%, or at about 80% poloxamer polymers.

In some embodiments, the pharmaceutical formulations of the present invention comprise poloxamer 407; the final concentration of poloxamer 407 in the formulation may range from about 2% to about 20% by weight, or by volume of the formulation; or from about 5% to about 20% by weight or by volume of the formulation, or from about 10% to about 20% by weight, by volume of the formulation, or from about 15% to about 20% by weight or by volume of the formulation. In some aspects, an antibiotic formulation may comprise 5.0%, 6.0%, 7.0%, 8.0%, 9.0%, 10.0%, 10.5%, 11.0%, 11.5%, 12.0%, 12.5%, 13.0%, 13.5%, 14.0%, 14.5%, 15.0%, 15.5%, 16.0%, 16.5%, 17.0%, 17.5%, 18.0%, 18.5%, 19.0%, 19.5% or 20.0% poloxamer 407 by weight or by volume of the formulation.

In other embodiments, the pharmaceutical formulations of the present invention may further comprise poloxamer 188; the final concentration of poloxamer 188 in the formulation may range from about 2% to about 30%; or from about 5% to about 15% by weight of the formulation, from about 5% to about 20% by weight or by volume of the formulation, or preferably from about 10% to about 20% by weight or by volume of the formulation.

Pharmaceutical formulations of the present invention further comprise at least one contrast agent. The contrast agent may be selected from the group consisting of Iohexol, Iopamidol, and Iopromide. By way of example, a pharmaceutical formulation according to the present invention may comprise about 30 to about 600 iodine per milliliter of the formulation solution, preferably about 50 to about 300, or about 75 to about 200 iodine per milliliter of the formulation solution.

In some embodiments, pharmaceutical formulations of the present invention further comprise one or more excipients that increase the solubility of antibiotic, such as linezolid. One example may be cyclodextrins. Cyclodextrins (also called cycloamyloses) are a family of cyclic oligosaccharides consisting of sugar molecules bound in a ring. Cyclodextrins are hydrophobic inside and hydrophilic outside. They have been used to complex with hydrophobic compounds to enhance the solubility and bioavailability of such compounds. Cyclodextrins may be Alpha-, beta-, and gamma-cyclodextrin which are all approved by FDA, or a mixture cyclodextrin. In some aspects, the composition may comprise about 15% to about 40% of cyclodextrin by weight or by volume of the composition. In one example, it may comprise about 20%, 25%, or 30% of cyclodextrin.

Other surfactants, solvents or co-solvents known to those of skill in the art may also be used in some embodiments within the scope of the invention. Those additional components may be used to adjust the PH value of the composition.

The thermosensitive hydrogel is an aqueous solution at low temperature but on warming provide stiff gels from which the antibiotics can diffuse. Over several days the gels breakdown. Formulations provide sustained and controlled release of the active agent. Varying the concentrations of components in the formulation can allow fine tuning of the properties of the gels such as solution-to-gel transition temperature.

In some embodiments, the formulations comprising thermosensitive poloxamer are aqueous solution having a lower critical solution temperature (LCST) of between 4° C. and 37° C., preferably between 4° C. and 25° C. The viscous solution has low viscosity at room temperature suitable for injection. The aqueous solution undergoes a sol-gel transition starting between 4° C. and 37° C. Preferably the soluble formulation may form gel at about 32° C. to about 40° C., or at about 35° C. to 38° C., or at about 36° C. to about 38° C., or at about 36° C. to about 37° C. The aqueous formulation may gel at 34° C., 35° C., 36° C., 37° C., 37° C., 38° C. or 39° C. In one sample, the aqueous formulation may gel at 37° C.

TABLE 1

Solution to gel transition temperature for poloxamer hydrogels

|  | Solution/gel transition temperature |
|---|---|
| Vancomycin/poloxamer | 36-37 |
| Linezolid/poloxamer | 32-34 |

The pharmaceutical formulation of the present invention may have an osmolality ranging from 100 to 1000 Osm/L, preferably from 200 to 900 Osm/L, more preferably from 400 to 600 Osm/L. For example, the formulation of the present invention may have an osmolality of 350 Osm/L, 400 Osm/L, 450 Osm/L, 500 Osm/L, 550 Osm/L, 600 Osm/L, 650 Osm/L, 700 Osm/L, 800 Osm/L, or 900 Osm/L.

In some embodiments, thermosensitive hydrogel formulations of the present invention may be administered to a disease site using a small size needle. The feature of the water solubility of thermogels at room temperature, and the relatively low viscosity of the aqueous solution makes the use of small-bore needles possible. Such injectable formulation can be effectively administered to a patient with a small size needle without exhibiting pre-gelation. Another feature of the thermosensitive gel formulations of the present invention is the ability to deliver therapeutically active agents at a controlled rate and without loss of biological activity. Such hydrogels formed inside the injection site can entrap substantial amounts of active agents at the injection site in the body for controlled release of the drug at the desired location.

In some embodiments, the thermogel polymers can be dissolved in an appropriate volume of an aqueous solution and the antibiotic is dissolved or suspended in the same solution prior to the injection. The mixture is then injected in the desired body site, where it gels, entrapping the antibiotic agent in the gelled materials.

III. Administration and Dosing

The pharmaceutical composition and/or formulation comprising at least one antibiotic of the present invention may be administered by any route which results in a therapeutically effective outcome. The exact amount required will vary from subject to subject, depending on the species, age, and general condition of the subject, the severity of the disease, the particular composition, its mode of administration, its mode of activity, and the like.

Parenteral or injectable administration producing a localized effective level of antibiotic (above MIC of target bacteria) has beneficial outcomes. According to the present invention, "parenteral" administration refers to a drug, medicine or therapeutic being administered, or administration occurring, anywhere in the body other than the mouth or alimentary canal. Injectable administration refers to any drug, medication or therapeutic which is injected.

This would reduce the level of side effects, increase patient compliance to the dosing regime and increase efficacy at the site of action with a smaller antibiotic dosage.

The advantages of parenteral or injectable dosage forms include relative ease of application, localized delivery for a site-specific action in the body, reduced dosing frequency without compromising the effectiveness of the treatment, increased dosing compliance, etc.

Pharmaceutical compositions in accordance with the invention are typically formulated in dosage unit form for ease of administration and uniformity of dosage. It will be understood, however, that administration of the pharmaceutical compositions of the present invention will be decided by the attending physician within the scope of sound medical judgment.

In accordance with the present invention, the pharmaceutical composition and/or formulation may comprise a total dose of 1.0 mg to 100 mg of vancomycin. In one aspect, the total dose is about 1.0 mg to about 50 mg of vancomycin, or about 1.0 mg to about 20 mg of vancomycin, or about 2.0 to about 10 mg of vancomycin, or about 2.0 mg to about 5.0 mg of vancomycin, or about 3.0 to about 6.0 mg of vancomycin. In other aspects, the pharmaceutical composition may comprise a total dose of 1.0 mg, 2.0 mg, 3.0 mg, 4.0 mg, 5.0 mg, 6.0 mg, 7.0 mg, 8.0 mg, 9.0 mg, 10 mg, 15 mg, 20 mg, 25 mg, 30 mg, 45 mg, 50 mg, or 100 mg of vancomycin. The vancomycin may be formulated as a salt or a free base.

In accordance with the present invention, the pharmaceutical composition and/or formulation may comprise a total dose of 1.0 mg to 500 mg of linezolid. In one aspect, the total dose is about 1.0 mg to about 20 mg of linezolid, or about 2.0 mg to about 5.0 mg of linezolid, or about 10 mg to about 100 mg of linezolid, or about 10 mg to about 200 mg of linezolid, or about 20 mg to about 200 mg of linezolid. In other aspects, the pharmaceutical composition may comprise a total dose of 1.0 mg, 2.0 mg, 3.0 mg, 4.0 mg, 5.0 mg, 6.0 mg, 7.0 mg, 8.0 mg, 9.0 mg, 10 mg, 15 mg, 20 mg, 25 mg, 30 mg, 45 mg, 50 mg, 60 mg, 70 mg, 80 mg, 90 mg, 100 mg, 200 mg, 300 mg, 400 mg, or 500 mg of linezolid.

The pharmaceutical composition and/or formulation comprising at least one antibiotic of the present invention may be administered to a patient using any amount and any route of administration effective for treating or preventing pain. The exact amount required will vary from subject to subject, depending on the species, age, and general condition of the subject, the severity of the disease, the particular composition, its route of administration, its mode of activity, the time of administration, rate of excretion of the specific antibiotic compound employed, the duration of the treatment, drugs used in combination or coincidental with the specific antibiotic compound employed, and like factors well known in the medical arts. Compositions in accordance with the invention are typically formulated in dosage unit form for ease of administration and uniformity of dosage. It will be understood, however, that the total usage of the compositions of the present invention may be decided by the attending physician within the scope of sound medical judgment.

In some embodiments, pharmaceutical compositions and formulations of the present invention may be administered at dosage levels sufficient to deliver from about 1 mg to a total of 1000 mg of the at least one antibiotic, to obtain the desired therapeutic effect. In some embodiments, the compositions may deliver less than 100 mg of the at least one antibiotic to obtain the desired therapeutic effect. In some embodiments, the compositions may deliver less than 50 mg of the at least one antibiotic to obtain the desired therapeutic effect. In some embodiments, the compositions may deliver less than 20 mg of the at least one antibiotic to obtain the desired therapeutic effect. Dosages may range from 1 mg to 2000 mg or even 5000 mg per active ingredient or in total where more than one active ingredient is present. Active ingredients when present as more than one compound may be present in the same amount, or in differing amounts. One active ingredient may be present at 5, 10, 20, 30, 40, 50, 60, 70, 80, 90 or 95% of a second or subsequent active ingredient. They may be between 1-10 mg, 1-25 mg, 1-50 mg, 1-100 mg, 1-250 mg, 1-500 mg, 1-1000 mg, 5-50 mg, 10-50 mg, 10-100 mg, 10-250 mg, 10-500 mg, 10-1000 mg, 25-100 mg, 25-250 mg, 25-500 mg, 100-250 mg, 100-500 mg, 100-1000 mg, 500-2000 mg, or 2000-5000 mg. In some embodiments, the dosage level is determined based upon the infected discs. Dosages may range from 1 mg to 500 mg for each infected disc.

In some embodiments, volume-based dosing strategy may be used. In other embodiments, a single administration (e.g., a single injection) is used to deliver a desired dosage of the antibiotic to the infected disc.

Liquid dosage forms for parenteral administration include, but are not limited to, pharmaceutically acceptable emulsions, microemulsions, solutions, suspensions, syrups, and/or elixirs. In addition to active ingredients, liquid dosage forms may comprise inert diluents commonly used in the art including, but not limited to, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures 15 thereof. In certain embodiments for parenteral administration, compositions may be mixed with solubilizing agents such as CREMOPHOR®, alcohols, oils, modified oils, glycols, polysorbates, cyclodextrins, polymers, and/or combinations thereof.

Injectable preparations, for example, sterile injectable aqueous or oleaginous suspensions, or injectable microparticles may be formulated according to the known art using suitable dispersing agents, wetting agents, and/or suspending agents. Sterile injectable preparations may be sterile injectable solutions, suspensions, and/or emulsions in non-toxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectable formulations.

Injectable formulations can be sterilized, for example, by filtration through a bacterial-retaining filter, by irradiation, by steam sterilization, and/or by incorporating sterilizing agents in the form of sterile solid compositions which can be dissolved or dispersed in sterile water or other sterile injectable medium prior to use.

In some embodiments, formulations and compositions of the present invention may be administered to a subject in need at or near the bone, joint, ligament and tendon by a single injection, or alternatively through multiple injections at more than one site. For example, formulations and compositions of the present invention may be injected into multiple vertebra discs from the same side of the spine, or from both sides of the spine. In other examples, formulations and compositions of the present invention may be injected into vertebra discs and vertebra disc space.

IV. Kits, Needles and Devices

Method and devices known in the art for multi-administration to cells, organs and tissues are contemplated for use in conjunction with the methods and compositions disclosed herein as embodiments of the present invention. These include, for example, those methods and devices having multiple needles, hybrid devices employing for example lumens or catheters as well as devices utilizing heat, electric current or radiation driven mechanisms.

Devices for administration may be employed to deliver pharmaceutical compositions comprising at least one antibiotic of the present invention according to single, multi- or split-dosing regimens taught herein. According to the present invention, these multi-administration devices may be utilized to deliver the single, multi- or split doses of antibiotics loaded in the formulations contemplated herein.

In some embodiments, devices for delivering medical agents have been described by Mckay et al. and are taught for example in PCT Patent Publication NO.: WO2006/118804, the contents of which are incorporated herein by reference in their entirety. According to Mckay, multiple needles with multiple orifices on each needle are incorporated into the devices to facilitate regional delivery to a tissue, such as the interior disc space of a spinal disc.

Devices containing the pharmaceutical composition comprising at least one antibiotic may be implanted at the site of pain to deliver the pharmaceutical composition to tissues around the site of implantation. Implantable devices may provide more localized administration of the pharmaceutical compositions than oral and topical administrations, while maintaining a low or negligible systemic level of the therapeutic agents. Various solid and semi-solid drug delivery implants are known, including polymeric and non-polymeric ones. Implants may be injected and it may be possible to deliver drugs into deeper tissue areas at time of surgery. Sites of implantation may include, but are not limited to, at, in or near a bone, joint, ligament, or tendon, an intervertebral space, an intra-articular space, a tendon and bone junction, and sites adjacent to bone edema.

In certain embodiments, the implantable devices are characterized by at least one polymeric ingredient. The implants may be erodible or biodegradable implants, such as those made with polyanhydrides or polylactides, or non-erodible or non-biodegradable implants, such as those made with ethylene vinyl acetate. The implants may be in the form of a mesh, pellets, or wafer.

Syringes using needles may be employed to administer the pharmaceutical formulations of the present invention. In some cases, the needle tips may be specialized for a particular injection purpose, such as spinal injection. Syringes for spinal injection may have a needle placed into a structure or space in the spine. The needle may have a bevel of any types from Quincke babcock, Sprotte, Whitacre, Greene, Pitkin and Tuohy. The shaft of the needle may be straight or curved, and be in a certain length suitable for placing the medications in a specific location in the spine. For examples. The syringe and needles may be designed as disclosed in U.S. Pat. Nos. 5,628,734; 6,500,153; 7,367,961; and 8,112,159; the contents of each of which are incorporated herein by reference in their entirety.

In some embodiments, the syringes and needles for administration of the pharmaceutical formulations of the present invention may contain special structures configured for mixing the components of the pharmaceutical formulations in situ. The syringe may include one, two, or more separate chambers in which the components of the pharmaceutical formulations are stored separately and are mixed right before the injection.

Definitions

Biocompatible: As used herein, the term "biocompatible" means compatible with living cells, tissues, organs or systems posing little to no risk of injury, toxicity or rejection by the immune system.

Biodegradable: As used herein, the term "biodegradable" means capable of being broken down into innocuous products by the action of living things.

Biologically active: As used herein, the phrase "biologically active" refers to a characteristic of any substance that has activity in a biological system and/or organism. For instance, a substance that, when administered to an organism, has a biological effect on that organism, is considered to be biologically active. In particular embodiments, a nucleic acid molecule of the present invention may be considered biologically active if even a portion of the nucleic acid molecule is biologically active or mimics an activity considered biologically relevant.

Formulation: As used herein, a "formulation" includes at least an active ingredient and a delivery agent.

Hydrogel: As used herein, the term "hydrogels" are viewed as water insoluble, crosslinked, three-dimensional networks of polymer chains plus water that fills the voids between polymer chains. Crosslinking facilitates insolubility in water and provides required mechanical strength and physical integrity. Hydrogel is mostly water (the mass fraction of water is much greater than that of polymer). The ability of a hydrogel to hold significant amount of water implies that the polymer chains must have at least moderate hydrophilic character.

LCST: As used herein, the term "LCST" refers to lower critical solution temperature (LCST) which is also known as gel temperature. In the context of the present invention, polymers are water-soluble below their LCST, but above the LCST, the chemical interaction between the hydrophobic domains of the polymer resulting in gelation of the polymer solution. The LCST value depends on the polymer compositions. Polymers having particular usefulness for therapeutic applications are those where the LCST value is between 20 and warm body temperature since such materials will be soluble in aqueous solutions at room temperature and form a gel at body temperature (37° C. for a human body for example.

Modic changes: As used herein, the term "modic change (MC)" refers to vertebral bone marrow lesions adjacent to degenerated discs that are specific for discogenic low back pain.

Patient: As used herein, the term "patient" refers to a subject who may seek or be in need of treatment, requires treatment, is receiving treatment, will receive treatment, or a subject who is under care by a trained professional for a particular disease or condition.

Pharmaceutical composition: As used herein, the phrase "pharmaceutical composition" refers to a composition that alters the etiology of a disease, disorder and/or condition.

Pharmaceutically acceptable: As used herein, the phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: As used herein, the phrase "pharmaceutically acceptable excipient" refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration.

Pharmaceutically acceptable salts: As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts can be synthesized from the parent compound which contains a basic or acidic moiety by conventional chemical methods. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

Pharmacokinetic: As used herein, the term "pharmacokinetic" refers to any one or more properties of a molecule or compound as it relates to the determination of the fate of substances administered to a living organism. Pharmacokinetics is divided into several areas including the extent and rate of absorption, distribution, metabolism and excretion. This is commonly referred to as ADME where: (A) Absorption is the process of a substance entering the blood circulation; (D) Distribution is the dispersion or dissemination of substances throughout the fluids and tissues of the body; (M) Metabolism (or Biotransformation) is the irreversible transformation of parent compounds into daughter metabolites; and (E) Excretion (or Elimination) refers to the elimination of the substances from the body. In rare cases, some drugs irreversibly accumulate in body tissue.

Pharmaceutically acceptable solvate: As used herein, the term "pharmaceutically acceptable solvate," as used herein, means a compound of the invention wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

Site: As used herein, the term "site", when used with respect to bone edema or Modic changes, means the site of bone edema or Modic change itself or an environment 0.5-1 inch around all directions of the bone edema.

Split dose: As used herein, a "split dose" is the division of single unit dose or total treatment dose into two or more doses.

Synthetic: The term "synthetic" means produced, prepared, and/or manufactured by the hand of man.

Therapeutic Agent: The term "therapeutic agent" refers to any agent that, when administered to a subject, has a therapeutic, diagnostic, and/or prophylactic effect and/or elicits a desired biological and/or pharmacological effect.

Therapeutically effective amount: As used herein, the term "therapeutically effective amount" means an amount of an agent to be delivered (e.g., antibiotic, drug, therapeutic agent, diagnostic agent, prophylactic agent, etc.) that is sufficient, when administered to a subject suffering from or susceptible to a disease, disorder, and/or condition, to treat, improve symptoms of, diagnose, prevent, and/or delay the onset of the disease, disorder, and/or condition.

Therapeutically effective outcome: As used herein, "therapeutically effective amount" means an amount of an agent to be delivered (e.g., antibiotic, drug, therapeutic agent, diagnostic agent, prophylactic agent, etc.) that is sufficient, when administered to a subject suffering from or susceptible to a disease, disorder, and/or condition, to treat, improve symptoms of, diagnose, prevent, and/or delay the onset of the disease, disorder, and/or condition.

Total treatment dose: As used herein, a "total treatment dose" is an amount given or prescribed in a treatment period. It may be administered as a single unit dose.

Treating: As used herein, the term "treating" refers to partially or completely alleviating, ameliorating, improving, relieving, delaying onset of, inhibiting progression of, reducing severity of, and/or reducing incidence of one or more symptoms or features of a particular disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any antibiotic, therapeutic or active ingredient; any method of production; any method of use; etc.) can be excluded from any one or more claims, for any reason, whether or not related to the existence of prior art.

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

EXAMPLES

Example 1: A Sheep Model of *S. aureus* Intradiscal Infection

A sheep model of *S. aureus* intradiscal infection has been developed to test the in vivo efficacy of antibiotic formulations. Male Charollais or Suffolk cross sheep, approximately 35-40 kg+ at the start of the study were housed according to Home Office guidelines under the Animals (Scientific Procedures) Act 1986 and acclimatised for at least 7 days with straw bedding and access to water. They were fed a Sheep concentrate diet without added antibiotics with additional forage (hay/straw) provided.

1.1 *Staphylococcus aureus* Infection

The bacterial inoculum (ATCC 29213) is prepared from frozen glycerol/phosphate-buffered saline stock at $2.5 \times 10^6$ CFU/ml by dilution to $2 \times 10^4$ CFU/ml:

1.2 Preparation of the Formulations for Injection 0.2 ml of the formulation is drawn up into the syringe using an 18G 1" or 1.5" needle. The syringe may be drawn back and forth to remove bubbles as necessary. The needle is then replaced with a 25G 4.69" administration needle, and primed leaving a dose of 0.1 ml. If not used immediately, the primed syringe is left in the fridge, but should be used within 30 minutes.

In a therapeutic model, each sheep is anesthetised and given four 0.05 ml (target volume) intradiscal Injections at L1/L2, L2/L3, L3/L4 and L4/5 of *S. aureus* inoculum ($1 \times 10^3$ cells/disc), one injection per disc.

Approximately 1 hour, or at another selected time, after the first injection, each sheep is given a second injection of the test formulation or control formulation. Each disc that was previously successfully injected with bacteria is given a 0.1 ml (target volume) intradiscal injection. As part of the anaesthesia the animal is given analgesics (intra-muscular) in the form of meloxicam at the recommended dosage. This analgesic may be repeated if considered necessary by the named veterinary surgeon. In a prophylactic model, the order of administrations is reversed such that the first injection is a formulation of antibiotic or control and the second injection contains the bacterial inoculum. The time between administration of the antibiotic and bacteria may be hours, days, weeks or months.

1.3 Injection Technique: Therapeutic Dosing.

Co-Localised Dosing

A single 20G 3.5" spinal needle is positioned directly into the edge of the nucleus pulposus of each disc. Following confirmation of positioning of the needles a second 25G 4.69" needle primed with the dose solution is inserted into the first needle and the tip placed into the middle of the nucleus pulposus. Following confirmation of positioning of the second needles each disc is injected with the bacteria. The inner needles will then be removed. Just prior to the 1 hour post-dose bacteria time-point a new 25G 4.69" needle, primed with the dose solution, is inserted into the 20G 3.5" and positioned into the middle of the nucleus pulposus. The second treatment is dose given via this needle, 1 hour post the first dose.

Discreet Dosing

Bacterial infection: A single 20G 3.5" spinal needle is positioned directly into the edge of the nucleus pulposus of each disc. Following confirmation of positioning of the needles a second 25G 4.69" needle primed with the dose solution is inserted into the first needle and the tip placed into the middle of the nucleus pulposus. Following confirmation of positioning of the second needles each disc is injected with the bacteria. The needles will then be removed. The animals are repositioned to access the other side of the spine.

Injection of formulation: A second 20G 3.5" spinal needle is positioned directly into the edge of the nucleus pulposus on the opposite side to the first injection of each disc. Just prior to time-point for administration a new 25G 4.69" needle, primed with the dose solution, is inserted into the 20G 3.5" and positioned into the middle of the nucleus pulposus. The second treatment is dose given via this needle.

For each injection, the individual dosing syringe is weighed and the weight recorded, pre and post-dosing to calculate the actual dose administered.

For each formulation the dose is given slowly, this should take 30 to 60 seconds to deliver, using enough force to successfully deliver the dose to the dose without causing any dose solution to leak out at the syringe/needle joint.

A digital x-ray imaging system will be used to aid injection and capture image records just prior to and post-dose. The animal will be continuously monitored and when fully recovered returned to their pen.

1.4 Injection Technique: Prophylactic Dosing

The order of the injections may be reversed such that the first injection is a formulation of antibiotic and the second injection contains the bacterial inoculum. The time between administration of the antibiotic and bacteria may be hours, days, weeks or months. The second injection may be co-localised or discreet e.g. injected on the same side of the disc as the first injection or injected on the other side of the disc to the first injection respectively.

1.5 Digital X-Ray Imaging

Each sheep is imaged and the image captured, just prior to and immediately after each dosing. Details of the sequences is recorded. A visual assessment of each IVD injection, immediately post-dose, is performed by a competent person. The injections will be scored/recorded as either: Good no leakage; Minimal leakage; Moderate leakage; Major leakage In order to ensure scientific robustness in the study ideally, four treated disc/group and a minimum three/group are required. After completing the injections for the sheep, the scores are reviewed. If less than the ideal number of discs in total are scored as "good no leakage" or "minimal leakage", the addition of extra sheep to this group, up to a maximum of 2 sheep, will be considered.

1.6 Tissue Samples

At set time-points post-dose the sheep is killed. The injected vertebrae discs are dissected out and the nucleus pulposus from each disc is removed. In addition, an extra untreated disc is sampled to provide control tissue. The disc is removed after all of the treated discs for the particular animal with care to ensure no contamination between control and treated samples.

Example 2: Vancomycin is More Effective when Therapeutically Dosed Co-Localised with the Bacterial Infection The sheep intradiscal infection model of Example 1 was used to evaluate the in vivo efficacy of therapeutically dosed vancomycin. The results indicate that without vancomycin treatment the $1 \times 10^3$ CFU of *S. aureus* injected into the discs proliferated to approximately $10^8$ CFU per gram of disc. Vancomycin formulated in Omnipaque containing 0.5% hyaluronic acid at 200 mg/ml vancomycin or 50 mg/ml vancomycin was injected one hour post infection as a co-localised or discreet injection.

When vancomycin administration was co-localised with the bacterial infection, all the discs were effectively sterilized within 24 h. Discs with undetectable levels of bacteria are plotted at 10 CFU/g of disc which is the limit of detection for the assay. When vancomycin was administered by discreet dosing 5 of 7 discs at 5 mg vancomycin/disc and 3 of 7 discs at 20 mg vancomycin/disc were sterilized. There does not seem to be a dose response and the results are consistent with the hypothesis that sterilized discs are the result of co-localised dosing e.g. injections from both sides of the disc resulted in the col-locaisation of bacteria and vancomycin. Although there were many sterile discs there was not a >3 $\log_{10}$ reduction in average bacterial burden in the discrete dosing groups.

Example 3: Vancomycin is More Effective when Dosed Prophylactically in the Sheep Intradiscal Infection Model The prophylactic model as described in Example 1 was used to test the hypothesis that vancomycin would be more effective if given time to diffuse throughout the disc prior to administration of the bacteria.

Discs were treated with vancomycin (5 mg/disc) on day 0 and on day 3 were discreetly infected with $10^3$ *S. aureus* per disc. 24 h after infection discs were harvested and bacterial burden was estimated. In control discs without vancomycin the *S. aureus* proliferated to $10^9$/g disc. There was an average reduction in bacterial burden in the vancomycin treated discs of >3 $\log_{10}$ which is considered to be highly significant and different to that obtained in therapeutic use of vancomycin (FIG. 1). This result is consistent with wider exposure to vancomycin throughout the disc achieved during the interval between vancomycin administration and bacterial infection.

The diffusional barrier the disc represents means that it may take longer for vancomycin to diffuse throughout the disc and to sterilize it but that it is possible to achieve this result. So the challenge is to get vancomycin into the disc and to keep it there for long enough to enable diffusion throughout the disc so that drug exposure is high enough to sterilise the disc.

One way to achieve this is to use a thermosensitive gel to ensure that the administered vancomycin (or other antibiotics) does not leak out of the disc through the needle hole or any fissures in degenerate discs. Studies that focus on thermosenstitive hydrogels to formulate antibiotics are designed to develop such formulations to improve antibiotic delivery and increase treatment efficacy.

Example 4: Vancomycin Formulation Development 4.1 Materials

The details of the active compound and the materials used in this study are listed in Table 2.

TABLE 2

Materials used in vancomycin formulations

| Compound Name | Abbreviations/ synonyms | Supplier | Batch/Lot number | Kuecept code |
|---|---|---|---|---|
| Vancomycin | Vanco | Wockhardt UK Limited Xellia Pharmaceuticals | L915 (API) A4250038 (clinical grade) | SYNS1406-672 |
| Poloxamer 407 | P407 | BASF | WPHF537D | |
| Omnipaque | | GE Healthcare | 12822236 | |
| Poloxamer 188 | P188 | BASF | WPWI603B | |
| Hydrochloric acid | | Aus titrinium | | 151300502 |
| Sodium hydroxide | | Analar Normapur | | 12E040024 |

4.2 Vancomycin Hydrogel Preparation and Formulation Development

Poloxamer hydrogels were prepared by the cold method as described elsewhere (Schmolka. Artificial skin. I. Preparation and properties of pluronic F-127 gels for treatment of burns. *Journal of Biomedical Materials Research*, 571-582, 1972). Vancomycin hydrochloride was added to Omnipaque at a final target concentration of 50 mg/mL, 75 mg/mL or 100 mg/mL. The drug solution was then stirred or sonicated (in ice) for approximately 2 hours until complete dissolution of the API and the pH adjusted to pH 6 with 1 M HCl and/or NaOH. Then, poloxamer 407 (w/w) or a combination of poloxamer 407 and poloxamer 188 (w/w) was added to the drug solution in order to achieve the desired polymer concentration. Formulations were kept in the fridge for 72 hours until a clear solution was obtained. In parallel, control samples were prepared and results compared with vancomycin loaded samples.

Over 30 vancomycin formulations were prepared and tested (Table 3). The purpose is to identify examples of each suitable for in vivo evaluation to provide proof of concept. The solution-to-gel transition temperature, transition time, injectability, solubility, and the concentration of final antibiotic were evaluated (Table 3).

4.3 Vancomycin Solution-Gel Transition Temperature Assessment

The thermoreversible behavior of the prepared formulations was visually assessed by a tube inversion method at different temperatures. Vials containing the prepared hydrogels were transferred to an incubator and the temperature increased at a rate of 2° C./10 minutes. At each increase in temperature, vials were removed from the incubator and inverted to assess the liquid-gel behavior.

Samples were classified accordingly to their rheological properties as: liquid (L) when moving rapidly in the direction of gravity, viscous liquid (VL) when it moved slowly and as a gel (G) when remaining on the bottom of the vial. The latter was classified as the sol-gel transition temperature. Mixtures of Poloxamers that were not soluble (NS).

4.4 Vancomycin Injectability/Syringeability Evaluation

Syringeability and injectability were assessed through a 25 gauge, 4.69 inch needle and parameters such as pressure/force required for injection and evenness of flow divided into 4 categories as follow: 1=injection: not possible; flow: no flow; 2=injection: difficult; flow: drop wise, 3=injection: moderate; flow: continuous; 4=injection: easy; flow: continuous. In addition, accuracy of dose measurements was performed by comparing the weight upon withdrawing 100 µL of each formulation through the syringe with and without the needle into a vial. It is noted that in some cases, injectability was assessed through a 25 gauge, 4.69 inch needle using a warm orange and classified as good, possible or not possible.

TABLE 3

Vancomycin formulations

| Final Vancomycin concentration (mg/ml) | Final Poloxamer 407 concentration (% w/w) | Additional excipients final concentration (w/w) | Physical state at 22° C. | Solution-GEL transition Tm (° C. range) | Injectability/ Solubility at 0 h/ 3 h at RT |
|---|---|---|---|---|---|
| 0 | 10 | — | Liquid | >36 | — |
| 0 | 14 | — | Liquid | >36 | — |
| 0 | 16 | — | Liquid | >36 | — |
| 0 | 18 | — | Liquid | >36 | — |
| 0 | 20 | — | Liquid | 20-36 | — |
| 47.5 | 5 | — | Liquid | >36 | — |
| 45 | 5 | Poloxamer188 5% | Liquid | >36 | — |
| 42.5 | 5 | Poloxamer188 10% | Liquid | >36 | — |
| 45 | 10 | — | Liquid | >36 | — |
| 42.5 | 10 | Poloxamer188 5% | Liquid | >36 | — |
| 40 | 10 | Poloxamer188 10% | Liquid | >38 | — |
| 37.5 | 10 | Poloxamer188 15% | Liquid | >36 | — |
| 20 | 10 | Poloxamer188 50% | Liquid | >36 | — |
| 37 | 11 | Poloxamer188 15% | Liquid | >36 | — |
| 36.5 | 11 | Poloxamer188 16% | Viscous Liquid | 36-37 | — |
| 36 | 11 | Poloxamer188 17% | Viscous Liquid | 30-32 | — |
| 35.5 | 11 | Poloxamer188 18% | Viscous Liquid | ≤30 | — |
| 35 | 11 | Poloxamer188 19% | Viscous Liquid | ≤30 | — |
| 34.5 | 11 | Poloxamer188 20% | Viscous Liquid | ≤36 | 1 |
| 27 | 11 | Poloxamer188 35% | Not Soluble | — | — |
| 44 | 12 | — | Liquid | 36-37 | 2/2 |
| 41.5 | 12 | Poloxamer188 5% | Liquid | >36 | — |
| 39 | 12 | Poloxamer188 10% | Liquid | >38 | — |
| 38 | 12 | Poloxamer188 12% | Liquid | >38 | — |
| 37 | 12 | Poloxamer188 14% | Viscous Liquid | >38 | — |
| 36 | 12 | Poloxamer188 16% | Viscous Liquid | 30-32 | — |
| 35 | 12 | Poloxamer188 18% | Viscous Liquid | ≤30 | — |
| 34 | 12 | Poloxamer188 20% | Viscous Liquid | ≤36 | 1 |
| 43.5 | 13 | — | Viscous Liquid | ≤30 | — |
| 43 | 14 | — | Liquid | 32-34 | 1 |
| 86 | 14 | — | Viscous Liquid | 36-37 | — |
| 64.5 | 14 | — | Viscous Liquid | <30 | — |
| 42.5 | 14 | Poloxamer188 1% | Viscous Liquid | <30 | — |
| 42 | 14 | Poloxamer188 2% | Viscous Liquid | <30 | — |
| 41.5 | 14 | Poloxamer188 3% | Liquid | 30-32 | 2 |
| 41 | 14 | Poloxamer188 4% | Liquid | 32-34 | 2 |
| 40.5 | 14 | Poloxamer188 5% | Liquid | 34-36 | 2 |
| 38 | 14 | Poloxamer188 10% | Liquid | 28-30 | 2/1 |
| 35.5 | 14 | Poloxamer 188 15% | Viscous Liquid | ≤30 | 1 |
| 30.5 | 14 | Poloxamer 188 25% | Not soluble | — | — |
| 28 | 14 | Poloxamer 188 30% | Not Soluble | — | — |
| 42 | 16 | — | Viscous Liquid | 26-28 | — |
| 84 | 16 | — | Viscous Liquid | 34-36 | — |
| 41 | 18 | — | Viscous Liquid | 26-28 | — |
| 82 | 18 | — | Viscous Liquid | 34-36 | — |
| Repeat batches | | | | | |
| 44 | 12 | — | Liquid | 36-37 | 2/2 |
| 44 | 12 | — | Liquid | 36-37 | 2/2 |
| 44 | 12 | — | Liquid | 36-37 | 2/2 |

4.5 Vancomycin Formulation Results

Previous work suggested that the rheological properties of vancomycin poloxamer 407 preparations at 25% and 30% (w/w) could restrict clinical administration. Therefore, there was a need to develop a formulation with better injectability/syringeability characteristics that could be delivered by intradiscal administration through a 25 gauge, 4.69 inch needle which is suitable for sheep injection. Formulation optimization work described herein employed poloxamer 407 concentrations from 5% to 18% (w/w) with or without the addition of poloxamer 188 (5% to 50% (w/w)).

The inverted tube method showed that poloxamer 407 preparations without vancomycin exhibited reversal thermal gelation, transforming from a liquid into a semisolid gel at a concentration of 20% (w/w) with a sol-gel transition temperature of 30° C. On the other hand, formulations at a poloxamer 407 concentration below 20% (w/w) did not exhibit gelation properties, behaving as a liquid or viscous liquid between 22° C. and 36° C. (Table 3).

The data suggest that the addition of vancomycin changes the sol-gel transition temperature of P 407 preparations (e.g. control 14% P 407 vs 14% P 407+43 mg/mL vancomycin). The decrease in sol-gel transition temperature was thought to be due to an interference in the polymer micellization process that promoted the creation of a cross-linked network at poloxamer concentrations below 18% (w/w).

When poloxamer 407 was employed as the delivery vehicle, sol-gel transition was only observed at a concentration equal or higher than 12% (w/w) (Table 3). In addition, increasing poloxamer 407 concentration was shown to decrease sol-gel transforming temperature (e.g. 12% poloxamer 407+44 mg/mL with a sol-gel temperature of 37° C. vs 13% poloxamer 407+43.5 mg/mL with a sol-gel temperature of 30° C.)

An increase in vancomycin drug load (43 mg/mL to 86 mg/mL and 42 mg/mL to 84 mg/mL at 14% and 16% (w/w), respectively) in the delivery vehicle was shown to result in an increase in sol-gel transition temperature (e.g. 36° C. to 37° C. and 28° C. to 36° C., respectively). Although an increase in sol-gel transition temperature close to physiological conditions was thought to be optimal from a formulation optimization perspective, visually observation suggests that an increase in viscosity may hinder clinical administration (e.g. formulation is liquid at a poloxamer 407 concentration of 14% (w/w) with a drug load of 43 mg/mL whereas it appears as a viscous liquid with a drug load of 86 mg/mL).

The data also indicates that the addition of poloxamer 188 to the vehicle resulted in an increase in viscosity and hence in a decrease in sol-gel transition temperature (e.g. 11% poloxamer 407+16% poloxamer 188 vs 11% poloxamer 407+17% poloxamer 188; 12% poloxamer 407 vs 12% poloxamer 407+12% poloxamer 407+18% poloxamer 407) (Table 2). Previous reports in the literature suggest that the addition of poloxamer 188 to P 407 gels increases the sol-gel transition temperature. In general, poloxamer 188 concentrations above 20% (w/w) were shown not to be soluble in the delivery vehicle In another study, vancomycin was switch to w/v formulations Vancomycin loaded poloxamer hydrogels were prepared by the cold method. Vancomycin hydrochloride was added to omnipaque at a final target concentration of 100 mg/mL. The drug solution was then stirred until complete dissolution of the API and the pH adjusted to pH 6 with 1 M NaOH. In order to prepare 10 mL of each formulation at a poloxamer 407 concentration of 16%, 16.25%, 16.5%, 16.75%, 17% (w/v) with a target drug load of 50 mg/mL, 1.6 g, 1.625 g, 1.65 g, 1.675 g, 1.7 g of polymer were added to 5 mL aliquots of the prepared drug solution. The volume was then made up to 10 ml with omnipaque or type I water and the formulations were kept at 4° C. for 11 days to promote polymer dissolution. Calculations for the conversion of w/w poloxamer concentration to w/v poloxamer for vancomycin hydrogel preparation are based on the assumption that a 12% (w/w) poloxamer concentration corresponds to 16% when converted to w/v (formulation density of 1.33 g/cm3): 12 g poloxamer/100 g formulation×1.33 g formulation/1 mL formulation=0.16×100=16% w/v poloxamer 407.

Example 5: Linezolid Formulation Development 5.1 Materials

The details of the active compound and the materials used in this study are listed in Table 5 as seen below.

TABLE 5

Materials used for Linezolid formulations

| Compound Name | Abbreviations/ synonyms | Supplier | Batch/Lot number | Kuecept code |
|---|---|---|---|---|
| Linezolid | LNZ | Fluorochem | FCA3092 | SYNS0516-713 |
| Poloxamer 407 | P407 | BASF | WPHF537D | |
| Omnipaque | | GE Healthcare | 12822236 | |
| Poloxamer 188 | | BASF | WPWI603B | |
| Hydrochloric acid | P188 | Aus titrinium | | 151300502 |
| Sodium hydroxide | | Analar Normapur | | 12E040024 |
| HPMC 606 | | Sigma Alrich | | S2BF3200V |
| PVP K30 | | Basf | | 37262124U0 |
| Tween 80 | | Aus titrinium | | 151300502 |
| $KH_2PO_4$ | | Alfa Aesar | | D052029 |
| Methanol (HPLC grade) | MEOH | VWR | | |

5.2 Linezolid Nanosuspension Preparation

Linezolid (molecular weight, 337.346 g/mol) was selected as the antibacterial test agent and the ability to develop poloxamer thermoreversible hydrogels was explored. To evaluate the ability to develop nanosuspensions with linezolid loadings of 50 and 200 mg/mL, the short term physical stability of formulations was assessed, including particle size, polydispersity and homogeneity. Different concentrations of poloxamer 407 and 188 were then added and sol-gel transition temperature and injectability/syringeability were evaluated.

High Performance Liquid Chromatography (HPLC) was used to assay for drug content and the method employed has been reported elsewhere (Khasia et al., *Journal of Pharmacy Research*, 5(8): 4115-4118, 2012). The details of the method used are listed below in table 6.

TABLE 6

HPLC for assaying Linezolid

| Analytical column | Phenomenex Luna 250*4.6 mm 5 μm |
|---|---|
| Part number | 37262124U0 |

TABLE 4 vancomycin formulations (w/v)

| Final Vancomycin concentration mg/ml | Final Poloxamer 407 concentration % (w/v) | Additional excipients Final concentration (w/w) | Physical state at 22° C. | Sol-Gel transition Temperature ° C. range | Injectability/ Solubility at 0 h/ 3 h at room temperature |
|---|---|---|---|---|---|
| 50 | 16 | — | Liquid | >38 | 2/2 |
| 50 | 16.25 | — | Liquid | 34-36 | 2/2 |
| 50 | 16.5 | — | Liquid | 34-36 | 2/2 |
| 50 | 16.75 | — | Liquid | 32-34 | 2/2 |
| 50 | 17 | — | Liquid | 32-24 | 2/2 |

TABLE 6-continued

HPLC for assaying Linezolid

| | |
|---|---|
| Column temperature | 30° C. |
| Mobile phase | MeOH:KH$_2$PO$_4$ buffer (35%:65%) |
| Flow rate | 1 ml/min |
| Injection volume | 20 µl |
| Detector | UV |
| Detection wavelength | 251 nm |
| Run time | 10 min |

An Agilent 1100 HPLC system equipped with diode array detector was used in this work. The samples were placed in HPLC amber vials and stored at room temperature throughout the experiments. Two standards were prepared (standard A and standard B) at 0.1 mg/ml in mobile phase and sonicated for ca. 45 min until complete dissolution of the API and then filtered with a 0.22 µm PTFE syringe filter prior being injected in the HPLC. A system suitability test (SST) was performed to assess the good performance of the system. Two blanks were injected in order to determine the quality of the baseline (i.e. to discard any matrix interference). Standard A was injected 5 times and standard B was injected twice and the mean area of the peak and the % RSD was calculated for both standards in order to evaluate the repeatability precision of the injections. Finally, the standard agreement was calculated as described by the following equation $$\text{standard agreement} = \frac{\text{Area}_A}{\text{Area}_B} \times \frac{\text{Conc}_B}{\text{Conc}_A}$$

Where Area$_A$ and Area$_B$ is the area under the peak of standards A and B, respectively and Conc$_A$ and Conc$_B$ is the concentration of the standards A and B, respectively.

5.3 Formulation Feasibility Testing

Nanosuspensions were produced by wet bead milling at 530 RPM for 8 hours by adding the API (50 mg/mL and 200 mg/mL) to the dispersion medium as detailed in Table 7.

TABLE 7

Nanosuspension linezolid load and dispersion medium composition

| Linezolid load (mg/mL) | Dispersion medium |
|---|---|
| 50 | 0.5% w/v HPMC 606, 0.5% w/v PVP K30 and 0.1% w/v Tween 80 in Omnipaque |
| 50 | 0.5% w/v HPMC 606, 0.5% w/v PVP K30 and 0.1% w/v Tween 80 in type I water |
| 50 | 0.5% w/v poloxamer 407 in Omnipaque |
| 200 | 0.5% w/v HPMC 606, 0.5% w/v PVP K30 and 0.1% w/v Tween 80 in Omnipaque |

Post preparation, the nanosuspensions were separated from the zirconia beads and stored in closed vials at room temperature and monitored after 2 hours and 24 hours for particle size and settling/agglomeration tendency by Dynamic Light Scattering. Briefly, 5 µL of each prepared formulation was diluted in 1 ml of type I water and derived count rate was monitored by using photon correlation spectroscopy (Malvern Nanoseries Zetasizer, Malvern Instruments Ltd., Malvern, UK). Measurements were taken at 25° C. at a scattering angle of 173°. Refractive index and viscosity constants were set at 1.458 and 60 mPa·s, respectively.

The prepared linezolid nanosuspensions in different dispersion media (as shown in Table 7) were measured for derived count rate and polydispesity index. Particle size and polydispersity index of the drug particles were measured after 2 and 24 hours of nanomilling by dynamic laser light scattering (Table 8). The average particle size of linezolid was found to be in the nanosized range for all test systems. The greater particle size (p<0.01) was detected with the higher drug load whereas the smaller particle size was registered when poloxamer 407 was used as the suspending agent (414.1±15.77 nm vs 250.5±33.7 nm).

Particle size in the different dispersion media was not statistically different (p>0.05) at 2 and 24 hours with a 50 mg/mL drug load. On the other hand, particle size was found to be significantly greater (p<0.0001) at 24 hours with a 200 mg/mL drug load. In addition, it should be noted that polydispersity index was high (>0.5) for the majority of the test systems. Ideally, a nanosuspension should display a polydispersity index below 0.3 in order to prevent agglomeration/sedimentation during storage. The dispersion medium (HPMC 606 0.5%; PVP K30 0.5%; Tween 80 0.1% w/v) in Omnipaque was taken forward in subsequent work since it presented a better particle size and polydispersity index when compared with the other media that contained Omnipaque.

TABLE 8

Derived count rate and polydispesity index

| Nanosuspension (drug load) | Dispersion medium | Time (hours) | Particle size (nm) | Polydispersity index |
|---|---|---|---|---|
| 50 mg/mL | (HPMC 606 0.5%; PVP K30 0.5%; Tween 80 0.1% w/v) in Omnipaque | 2 | 337.4 ± 29.5 | 0.65 ± 0.02 |
| 50 mg/mL | (HPMC 606 0.5%; PVP K30 0.5%; Tween 80 0.1% w/v) in Omnipaque | 24 | 393.2 ± 33.45 | 0.71 ± 0.09 |
| 50 mg/mL | (HPMC 606 0.5%; PVP K30 0.5%; Tween 80 0.1% w/v) in H$_2$O | 2 | 388.4 ± 87.7 | 0.49 ± 0.12 |
| 50 mg/mL | (HPMC 606 0.5%; PVP K30 0.5%; Tween 80 0.1% w/v) in H$_2$O | 24 | 446.9 ± 90.3 | 0.47 ± 0.1 |
| 50 mg/mL | 5% (w/w) poloxamer 407 in Omnipaque | 2 | 250.5 ± 33.7** | 0.81 ± 0.01 |
| 50 mg/mL | 5% (w/w) poloxamer 407 in Omnipaque | 24 | 316.7 ± 78.4 | 0.73 ± 0.16 |

TABLE 8-continued

Derived count rate and polydispesity index

| Nanosuspension (drug load) | Dispersion medium | Time (hours) | Particle size (nm) | Polydispersity index |
|---|---|---|---|---|
| 200 mg/mL | (HPMC 606 0.5%; PVP K30 0.5%; Tween 80 0.1% w/v) in Omnipaque | 2 | 414.1 ± 15.77 | 0.53 ± 0.11 |
| 200 mg/mL | (HPMC 606 0.5%; PVP K30 0.5%; Tween 80 0.1% w/v) in Omnipaque | 24 | 978.1 ± 23.1*** | 0.61 ± 0.09 |

(p < 0.01 vs 200 mg/mL at 24 h; *p < 0.0001)

5.4 Linezolid Formulation Development

Poloxamer hydrogels were prepared by the cold method as described elsewhere (Schmolka, *Journal of Biomedical Materials Research*, 571-582, 1972). Poloxamer 407 (w/w) or a combination of poloxamer 407 and 188 (w/w) were gradually added to the prepared nanosuspensions kept at 4° C. under stirring. Formulations were stored in the fridge for 72 hours until a clear solution was obtained. In parallel, control samples were prepared and results compared with linezolid loaded samples.

Over 30 linezolid formulations were prepared and tested (Table 9). The purpose is to identify examples of each suitable for in vivo evaluation to provide proof of concept. The solution-to-gel transition temperature, transition time, injectability, solubility, and the concentration of final antibiotic were evaluated (Table 9).

5.5 Linezolid Sol-Gel Transition Temperature

Thermoreversible behavior of the prepared linezolid formulations were visually assessed by tube inversion method at different temperatures. Vials containing the prepared hydrogels were transferred to an incubator and the temperature increased from 2° C./10 min. At each two-degree increase in temperature, vials were removed from the incubator and inverted to assess the liquid-gel behavior.

Samples were classified accordingly to their rheological properties as: liquid (L)—when moving rapidly in the direction of gravity, viscous liquid (VL)—when moving slowly down in the direction of gravity and as a gel (G)—when remaining on the bottom of the vial. The latter was classified as the sol-gel transition temperature (Table 9).

5.6 Linezolid Formulation Injectability/Syringeability

Syringeability and injectability were assessed through a 25 gauge 4.69 inch needle upon storing the formulations in close vials for 30 minutes at room temperature. Parameters such as pressure/force required for injection and evenness of flow were divided into 4 categories: 1=injection: not possible; flow: no flow; 2=injection: difficult; flow: drop wise, 3=injection: moderate; flow: continuous; 4=injection: easy; flow: continuous (Table 9). In addition, accuracy of dose measurements was performed by comparing the weight upon withdrawing 100 µL of each formulation through the syringe with and without the 25 gauge 4.69 inch needle into a vial. It should be noted that in some cases, injectability was assessed through a 25 gauge 4.69 inch needle using a warm orange and classified as good, difficult, possible or not possible.

5.7 Statistical Analysis

Statistical evaluation was carried out using a statistical package for social sciences software (SPSs version 16.0, SPSS Inc., Chicago, USA). All data were analyzed by Student's t-test. Statistically significant differences were defined when $p<0.05$. Values were expressed as mean±standard deviation (SD) n=3.

TABLE 9

Linezolid formulations

| Final Linezolid concentration (mg/ml) | Final Poloxamer 407 concentration (% w/w) | Additional excipients final concentration (w/w) | Physical state at 22° C. | Solution-GEL transition Tm (° C. range) | Injectability/ Solubility at 0 h/ 3 h at RT |
|---|---|---|---|---|---|
| 0 | 10 | — | Liquid | >36 | — |
| 0 | 14 | — | Liquid | >36 | — |
| 0 | 16 | — | Liquid | >36 | — |
| 0 | 18 | — | Liquid | >36 | — |
| 0 | 20 | — | Liquid | 26-30 | — |
| 45 | 10 | — | Liquid | >36 | — |
| 180 | 10 | — | Liquid | >36 | — |
| 42.5 | 10 | Poloxamer188 5% | Liquid | >36 | — |
| 40 | 10 | Poloxamer188 10% | Liquid | >36 | — |
| 37.5 | 10 | Poloxamer188 15% | Liquid | >36 | — |
| 37 | 10 | Poloxamer188 16% | Liquid | >38 | — |
| 36.5 | 10 | Poloxamer188 17% | Liquid | 30-32 | 1 |
| 36 | 10 | Poloxamer188 18% | Liquid | 30-32 | 1 |
| 35.5 | 10 | Poloxamer188 19% | Viscous Liquid | <30 | — |
| 35 | 10 | Poloxamer188 20% | Viscous Liquid | ≤30 | — |
| 32.5 | 10 | Poloxamer188 25% | Not Soluble | — | — |
| 30 | 10 | Poloxamer188 30% | Not Soluble | — | — |
| 42 | 11 | Poloxamer188 5% | Liquid | >36 | — |
| 39 | 11 | Poloxamer188 11% | Liquid | >38 | — |
| 38.5 | 11 | Poloxamer188 12% | Viscous Liquid | >38 | — |
| 38 | 11 | Poloxamer188 13% | Viscous Liquid | >38 | — |

TABLE 9-continued

Linezolid formulations

| Final Linezolid concentration (mg/ml) | Final Poloxamer 407 concentration (% w/w) | Additional excipients final concentration (w/w) | Physical state at 22° C. | Solution-GEL transition Tm (° C. range) | Injectability/ Solubility at 0 h/ 3 h at RT |
|---|---|---|---|---|---|
| 37.5 | 11 | Poloxamer188 14% | Viscous Liquid | >38 | — |
| 37 | 11 | Poloxamer188 15% | Not Soluble | — | — |
| 32 | 11 | Poloxamer188 25% | Not Soluble | — | — |
| 29.5 | 11 | Poloxamer188 29.5% | Not Soluble | — | — |
| 44 | 12 | — | Liquid | >38 | — |
| 43 | 12 | Poloxamer188 2% | Liquid | >36 | — |
| 42 | 12 | Poloxamer188 4% | Liquid | >36 | — |
| 41.5 | 12 | Poloxamer188 5% | Liquid | >38 | — |
| 39 | 12 | Poloxamer188 10% | Liquid | 34-36 | 2 |
| 43.5 | 13 | — | Liquid | 32-34 | 2/2 |
| 43 | 14 | — | Liquid | 30-32 | 1 |
| 172 | 14 | — | Viscous Liquid | 30-32 | — |
| 40.5 | 14 | Poloxamer188 5% | Liquid | 32-34 | 1 |
| 38 | 14 | Poloxamer188 10% | Viscous Liquid | 26-28 | 1 |
| 42 | 16 | — | Viscous Liquid | 30-32 | — |
| 168 | 16 | — | Viscous Liquid | 30-32 | — |
| Repeat Batches | | | | | |
| 43.5 | 13 | — | Liquid | 32-34 | 2/2 |
| 43.5 | 13 | — | Liquid | 32-34 | 2/2 |
| 43.5 | 13 | — | Liquid | 32-34 | 2/2 |

5.8 Linezolid Formulation Results

The inverted tube method showed that placebo poloxamer 407 preparations displayed thermoreversible properties, transforming from liquid into a semisolid gel at a concentration of 20% (w/w) with a sol-gel transition temperature of 30° C. On the other hand, formulations at a concentration below 20% (w/w) did not exhibit reversal thermal gelation, behaving as a liquid or viscous liquid between 22° C. and 36° C. (Table 9), The data suggest that the addition of linezolid decreases the sol-gel transition temperature of poloxamer 407 preparations (e.g. control 16% poloxamer 407 vs 16% poloxamer 407+50 mg/mL linezolid).

When poloxamer 407 was employed as the delivery matrix with linezolid, a sol-gel transition temperature (32° C.-34° C.) was observed at a concentration between 13%-16% (w/w) (Table 4). In addition, increasing poloxamer 407 concentration was shown to decrease sol-gel transforming temperature (e.g. 13% poloxamer 407+43.5 mg/mL with a sol-gel temperature of 34° C. vs 14% poloxamer 407+43 mg/mL with a sol-gel temperature of 32° C. Increasing linezolid drug load in the delivery vehicle did not alter formulation rheological properties and sol-gel transition temperature (e.g. 14% poloxamer 407+43 mg/ml linezolid and 172 mg/ml linezolid, and 16% poloxamer 407+42 mg/ml linezolid and 168 mg/ml linezolid, the sol-gel temp was 32° C.).

In general, the addition of poloxamer 188 to the vehicle resulted in an increase in viscosity and a decrease in sol-gel transition temperature (e.g. 10% poloxamer 407 (w/w)+16% poloxamer 188 (w/w) vs 10% poloxamer 407 (w/w)+17% poloxamer 188 (w/w); 14% poloxamer 407 (w/w) vs 14% poloxamer 407 (w/w)+10% poloxamer 407 (w/w)) (Table 5). However, it should be noted that there was an increase in sol-gel transition temperature when 5% (w/w) poloxamer was employed with 14% (w/w) poloxamer 407 (Table 9).

Nanosuspensions were produced by wet bead milling at 530 RPM for 12 hours by adding linezolid form II (100 mg/mL) to Omnipaque that contained a suspending agent (HPMC 1% w/v, PVP K30 1% w/v) and a surfactant (Tween 80 0.2% w/v). Post preparation, the nanosuspensions were separated from the zirconia beads and poloxamer hydrogels were prepared by the cold method as described elsewhere (Schmolka. Artificial skin. I. Preparation and properties of pluronic F-127 gels for treatment of burns. Journal of Biomedical Materials Research, 571-582, 1972). In order to prepare 10 mL of each formulation at a poloxamer 407 concentration of 17.3%, 17.8%, 18.05%, 18.3%, 18.55% and 18.8% (w/v) with a target drug load of 50 mg/mL, 1.73 g, 1.78 g, 1.805 g, 1.83 g, 1.85 g and 1.88 g of polymer were added to 5 mL aliquots of the prepared suspension. The volume was then made up to 10 ml with type I water and the formulations were kept at 4° C. for 11 days to promote polymer dissolution. Calculations for the conversion of w/w poloxamer concentration to w/v poloxamer for linezolid hydrogel preparation are based on the assumption that a 13% (w/w) poloxamer concentration corresponds to 17.3% when converted to w/v (formulation density of 1.33 g/cm3): 13 g poloxamer/100 g formulation×1.33 g formulation/1 mL formulation=0.173×100=17.3% w/v poloxamer 407.

TABLE 10

Linezolid formulations (w/v)

| Final Linezolid concentration (mg/ml) | Final Poloxamer 407 concentration (w/v) | Additional excipient final concentration (w/v) | Physical state at 22° C. | Sol-gel transition temperature ° C. range | Injectability/ solubility at 0 h/ 3 h at room temperature |
|---|---|---|---|---|---|
| 50 | 17.3 | — | Liquid | >38 | — |
| 50 | 17.8 | — | Liquid | >38 | — |

TABLE 10-continued

Linezolid formulations (w/v)

| Final Linezolid concentration (mg/ml) | Final Poloxamer 407 concentration (w/v) | Additional excipient final concentration (w/v) | Physical state at 22° C. | Sol-gel transition temperature ° C. range | Injectability/ solubility at 0 h/ 3 h at room temperature |
|---|---|---|---|---|---|
| 50 | 18.05 | — | Liquid | >38 | — |
| 50 | 18.3 | — | Liquid | 34-36 | 2/2 |
| 50 | 18.55 | — | Liquid | 34-36 | 2/2 |
| 50 | 18.8 | — | Liquid | 34-37 | 2/2 |

Example 6: Screening Solubilizing Excipients for Linezolid

Linezolid is moderate water-soluble and forms a suspense of micro/nano crystals in most formulations. Different excipients are screened for their capacity of solubilizing linezolid. The solubility of linezolid crystal forms II and III in the presence of a variety of excipients was tested in water. Linezolid (~10 mg/ml lots) was added to the excipients and allowed to dissolve into solution. If a clear solution was obtained another lot of linezolid was added. This process continued until a saturated solution was obtained. The solution was filtered and the quantity of soluble linezolid was estimated using a quantitative HPLC-UV assay. The mass of linezolid added and soluble linezolid concentrations are shown below in Table 11. The target was to achieve >50 mg/ml soluble linezolid. The excipient screen identified Kleptose, Captisol, PEG300 and PEG400 as the most solubilising excipients. The solubility for Kleptose® and Captisol® (20 and 30% w/v) in 50% Omnipaque (w/v) solution at 37° C. is shown in Table 12. The Captisol® 20% and 30% w/v solutions saturated at approximate 30 and 40 mg/mL, respectively. Kleptose® 20 and 30% w/v showed a higher solubility for both the forms so far with 40 and 50 mg/mL, respectively. In particular, 30% Kleptose (w/v) can solubilize linezolid to the target >50 mg/ml in 50% Omnipaque (v/v).

TABLE 11 screening excipients to solubilize linezolid

| | Solubility (mg/mL) | | | |
|---|---|---|---|---|
| Excipients | Linezolid II (saturated) | Linezolid II Soluble | Linezolid III (saturated) | LinezSolubleolid III |
| 40% Captisol (w/v) | 57.45 | 47.45 | 58.05 | 48.05 |
| 40% Kleptose (w/v) | 78.23 | 68.23 | 77.57 | 67.57 |
| 10% Solutol (w/v) | 20.03 | 10.03 | 20.25 | 10.25 |
| 30% Solutol (w/v) | 19.85 | 9.85 | 20.06 | 10.06 |
| 30% PEG 400 + 0.5% Tween 80 + 5% Propylene glycol | 29.54 | 19.54 | 29.00 | 19.00 |
| PEG 400 | 40.13 | 30.13 | 39.07 | 29.07 |
| Propylene Glycol | 20.92 | 10.92 | 21.35 | 11.35 |
| PEG 300 | 30.32 | 20.32 | 41.72 | 31.72 |
| Cremophor | 10.18 | nil | 10.00 | Nil |
| Poloxamer | 10.34 | nil | 10.20 | Nil |
| Tween 80 | 10.37 | nil | 10.03 | Nil |

TABLE 12

Solubiliiy of Kleptose ® and Captisol ®

| | Solubility (50% Omnipaque) | | | |
|---|---|---|---|---|
| | FII Saturated solution | FIII | FII Solubility ca. (mg/mL) | FIII |
| Kleptose 20% | 50.04 | 49.79 | 40.04 | 39.79 |
| Kleptose 30% | 60.54 | 60.94 | 50.54 | 50.94 |
| Captisol 20% | 30.31 | 30.31 | 20.31 | 20.31 |
| Captisol 30% | 40.21 | 39.85 | 30.21 | 29.85 |

Data from the comnitued solubility experiment indicate that for Linezolid Form III Captisol 30% (w/v) can solubilize linezolid to 52.5 mg/ml and Kleptose at 20% and 30% (w/v) can achieve 53.9 and 66.4 mg/ml soluble linezolid, respectively.

Example 7: Linezolid Formulations with Cyclodextrin

Thermosensitive hydrogel formulations containing Linezolid, Kleptose or Captosol, Omnipaque and poloxamer 407 are prepared and tested for suitable sol-gel transition. Poloxamer 407 or a combination of poloxamer 407 and 188 hydrogels are prepared using the cold method as described in Example 6. Kleptose or Captisol at a concentration from 20% to 30% is added to the poloxamer solution. Linezolid crystals (e.g., Form II and form III) are added to the solution containing Kleptose or Captisol until linezolid is completely dissolved into the solution. Formulations are stored in the fridge for 72 hours until a clear solution is obtained or alternatively can be rapidly mixed using high shear to enable dissolution within hours. In parallel, control samples are prepared and results compared with linezolid loaded samples.

The sol-gel transition temperature is evaluated using the method described in Example 6. Thermoreversible behavior of the prepared linezolid formulations are visually assessed by tube inversion method at different temperatures. Vials containing the prepared hydrogels are transferred to an incubator and the temperature increased from 2° C./10 min. At each two-degree increase in temperature, vials are removed from the incubator and inverted to assess the liquid-gel behavior.

The injectability/syringeability of formulations is evaluated using the method described in Example 6. Syringeability and injectability are assessed through a 25 gauge 4.69 inch needle upon storing the formulations in close vials for 30 minutes at room temperature. Parameters such as pressure/force required for injection and evenness of flow were divided into 4 categories: 1=injection: not possible; flow: no flow; 2=injection: difficult; flow: drop wise, 3=injection: moderate; flow: continuous; 4=injection: easy; flow: continuous.

Figure 2:
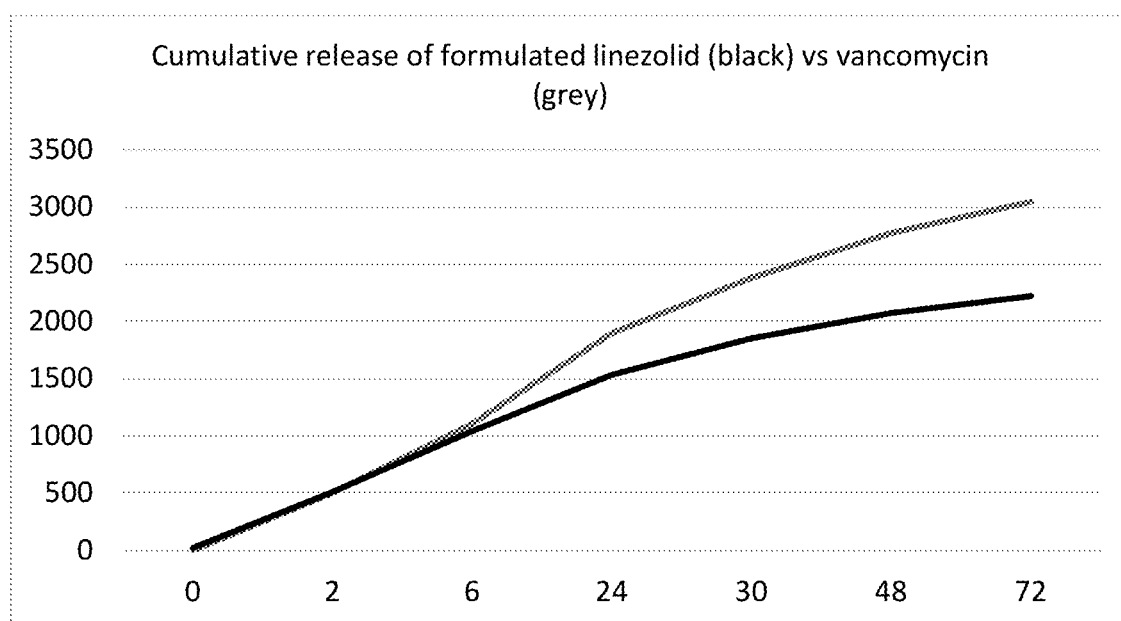
FIG. 2 shows a representative cumulative release of vancomycin and linezolid formulated in poloxamer hydrogels.

Example 8: In Vitro Diffusion and Release from Poloxamer Gels 100 microliters of poloxamer formulation were embedded in an agar disc. The release of loaded compound into media around the agar structure is measured. The assays mimic a disc containing a poloxamer injection. The mass of antibiotic released over 72 h was determined using high-performance liquid chromatography (HPLC). As shown in FIG. 2, 92% of the input vancomycin (gray) and 57% of input linezolid (black) was accounted for after 72 h. The dissolution and subsequent diffusion of linezolid may contribute to an element of modest sustained release in this formulation.

In vitro release assays indicate that vancomycin and linezolid formulated in poloxamer hydrogels are released from the gels.

The injectability of the hydrogels was determined both in vitro and ex vivo to ensure that the hydrogels were suitable for in vivo evaluation. After being removed from fridge storage, both vancomycin and linezolid formulations remain liquid and injectable for up to 3 h at Room Temperature.

Example 9: In Vivo Diffusion and Efficacy of Poloxamer Formulations Using an Infection Model The *S. aureus* spinal disc infection model of Example 1 with therapeutic dosing was used for this study.

Figure 3:
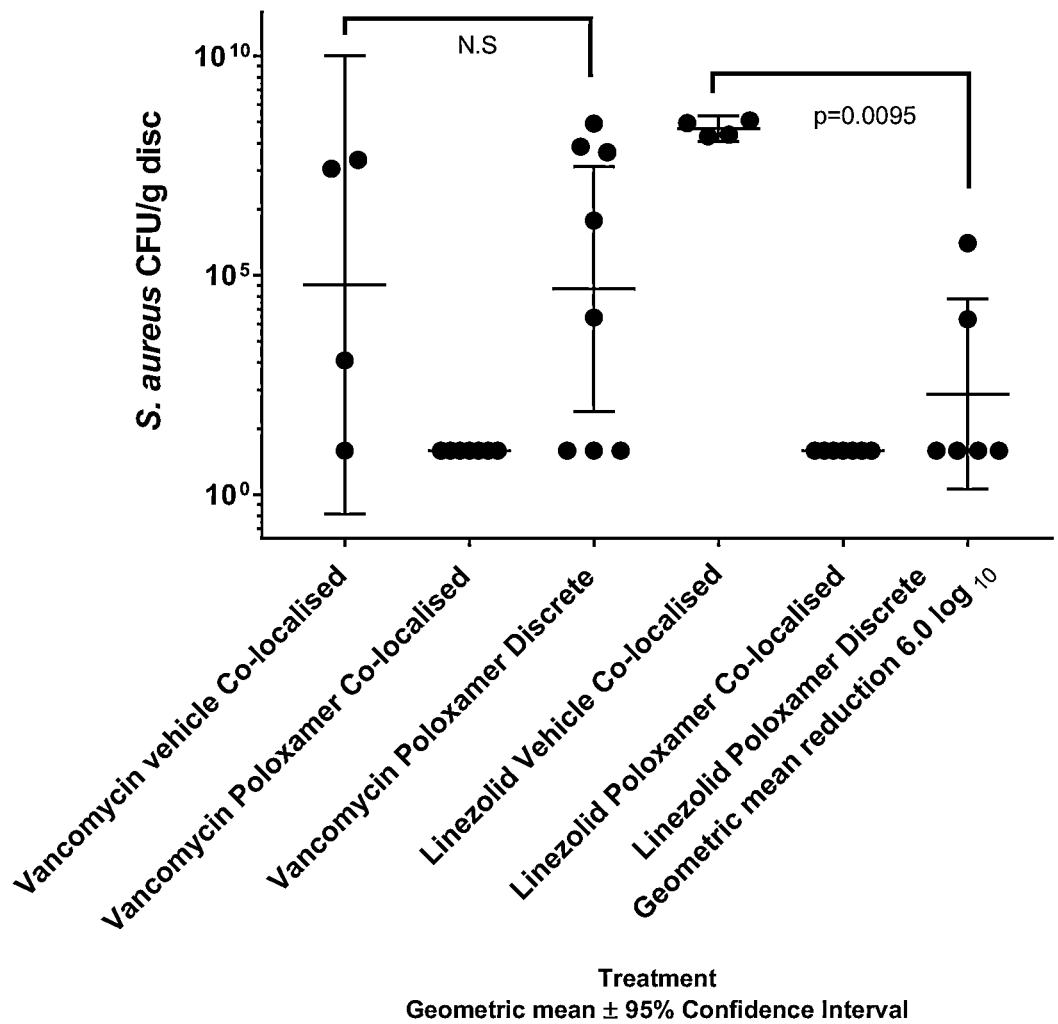
FIG. 3 shows the assessment of bacteria *S. aureus* burden per disc when dosed with linezolid and vancomycin in different formulations in a therapeutical model.
Figure 4:
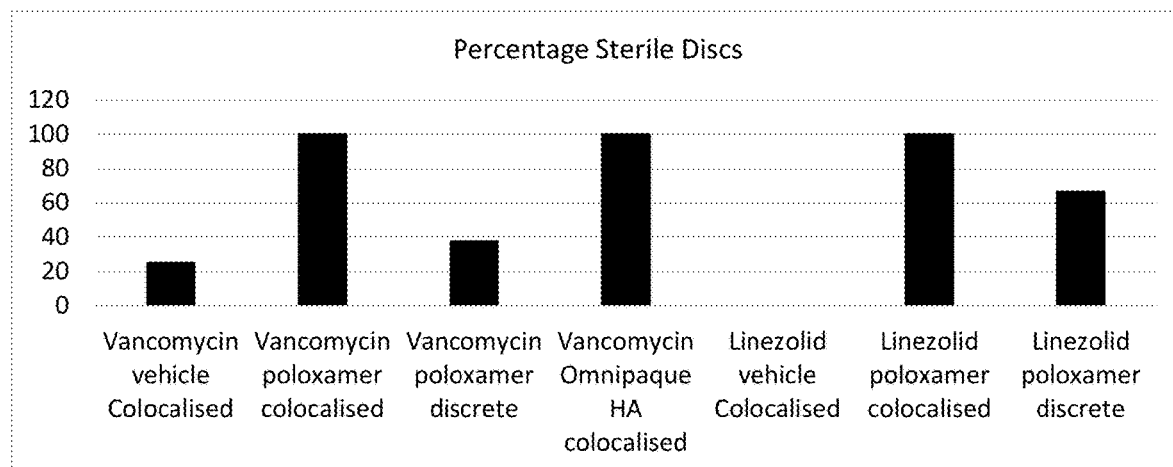
FIG. 4 is a histogram of percentage of sterile discs when dosed with linezolid and vancomycin in different formulations.

As shown in FIG. 3 and FIG. 4, when dosing is co-localized, vancomycin in omnipaque/HA or poloxamer reduced bacterial burden by >6 logs with all treated discs being effectively sterilized. When dosed discretely, from the other side of the disc, vancomycin did not significantly reduce average bacterial disc burden. One of four discs that received poloxamer vehicle alone was sterile and 3 of 8 discretely treated with vancomycin were sterile. In this study vancomycin was dosed therapeutically not prophylacticly and may not be expected to demonstrate a >3 $\log_{10}$ reduction in bacterial burden. The poloxamer formulation does not appear to increase the diffusion of vancomycin through the disc in this therapeutical model. Poloxamer formulated vancomycin is being tested in a prophylactic model of infection.

Linezolid in poloxamer sterilized all discs when co-localized with the bacteria (FIG. 3). Discrete dosing of linezolid in poloxamer led to a significant >3 $\log_{10}$ reduction in average disc burden with 4 of 6 discs sterilized. Clinically infected discs contain relatively few bacteria and a 3 $\log_{10}$ reduction within 24 h of treatment would lead to effective sterilization in most cases.

These results indicate that in a therapeutic model of *S. aureus* intradiscal infection, the linezolid poloxamer formulation was superior to the vancomycin poloxamer formulation.

The invention claimed is:

1. A method of treating lower back pain in a subject, the method comprising administering to the subject an injectable pharmaceutical composition, wherein the injectable pharmaceutical composition comprises:
    (a) an effective amount of linezolid, wherein the linezolid is present in an amount of from about 2.5% to about 20% by weight of the injectable pharmaceutical composition;
    (b) a thermosensitive hydrogel which is poloxamer 407, wherein said poloxamer 407 is present in an amount of from about 2% to about 20% by weight of the injectable pharmaceutical composition;
    (c) a radio-contrast agent iohexol; and
    (d) optionally, at least one pharmaceutically acceptable excipient;
wherein the linezolid forms a micro suspension or a nano-suspension in the injectable pharmaceutical composition, and wherein the injectable pharmaceutical composition is administered to the subject by injection to a lumbar intervertebral disc and/or the adjacent vertebrae or joints.

2. The method of claim 1, wherein the injectable pharmaceutical composition comprises an aqueous solution of poloxamer 407, wherein the linezolid is suspended therein, at a temperature of from about 4° C. to about 25° C.

3. The method of claim 2, wherein the aqueous solution gels a gel at a temperature of from about 32° C. to about 38° C.

4. The method of claim 1, wherein the aqueous solution remains liquid for at least 3 hours at room temperature.

5. The method of claim 1, wherein the injectable pharmaceutical composition comprises a total dose of from about 1 mg to about 200 mg of linezolid.

6. The method of claim 5, wherein the injectable pharmaceutical composition comprises a total dose of from about 20 mg to about 200 mg of linezolid.

7. The method of claim 6, wherein the total dose of from about 20 mg to about 200 mg of linezolid is administered to the subject in two or more doses.

8. The method of claim 1, wherein the injectable pharmaceutical composition comprises a total dose of from about 10 mg to about 500 mg of linezolid.

9. The method of claim 1, wherein the poloxamer 407 is present in an amount of from about 5% to about 20% by weight of the injectable pharmaceutical composition.

10. The method of claim 1, wherein the injectable pharmaceutical composition remains in the lumbar intervertebral disc and/or the adjacent vertebrae or joints at a sufficient concentration and for a duration sufficient for the linezolid to provide an antibacterial effect.

11. The method of claim 1, wherein the injectable pharmaceutical composition remains in the lumbar intervertebral disc and/or the adjacent vertebrae or joints for a duration sufficient for the linezolid to diffuse into a disc tissue.

12. The method of claim 1, wherein the linezolid diffuses into the lumbar intervertebral disc and/or the adjacent vertebrae or joints by controlled release.

13. The method of claim 1, wherein the adjacent vertebrae are thoracic, lumbar, or sacral vertebrae.

14. The method of claim 1, wherein the injectable pharmaceutical composition has a sol-gel transition temperature of from about 32° C. to about 34° C.

15. The method of claim 1, wherein the injectable pharmaceutical composition is administered to the subject through multiple injections at more than one site.

16. The method of claim 1, wherein the injectable pharmaceutical composition is administered to the subject in two or more doses.

17. The method of claim 1, wherein the injectable pharmaceutical composition is sterilized by one or more of filtration through a bacterial-retaining filter, irradiation, steam sterilization, and/or incorporation of sterilizing agents in the form of sterile solid compositions.

18. The method of claim 1, wherein the injection comprises:
  positioning a first needle into the lumbar intervertebral disc and/or the adjacent vertebrae or joints;
  inserting a second needle primed with the injectable pharmaceutical composition into the first needle; and
  injecting the injectable pharmaceutical composition through the second needle.

19. The method of claim 1, further comprising administering an analgesic to the subject.

20. The method of claim 1, wherein the injection is percutaneous.

21. A method of simultaneously (1) relieving or ameliorating lower back pain in a subject and (2) eliminating a bacterial infection in a lumbar intervertebral disc, lumbar intervertebral space and/or lumbar vertebra in the subject, the method comprising administering to the subject an injectable pharmaceutical composition, wherein the injectable pharmaceutical composition comprises:

(a) an effective amount of linezolid, wherein the linezolid is present in an amount of from about 2.5% to about 20% by weight of the injectable pharmaceutical composition;

(b) a thermosensitive hydrogel which is poloxamer 407, wherein said poloxamer 407 is present in an amount of from about 2% to about 20% by weight of the injectable pharmaceutical composition;

(c) a radio-contrast agent iohexol; and (d) optionally, at least one pharmaceutically acceptable excipient;

wherein the linezolid forms a micro suspension or a nano-suspension in the injectable pharmaceutical composition, and wherein the injectable pharmaceutical composition is administered to the subject by injection to a lumbar intervertebral disc and/or the adjacent vertebrae or joints.

* * * * *